US012756332B2

(12) United States Patent
Reitz et al.

(10) Patent No.: US 12,756,332 B2
(45) **Date of Patent: *Oct. 6, 2026**

(54) ELECTROSTATIC MACHINE SYSTEM HAVING A DIELECTRIC FLUID AND A METHOD OF OPERATION OF THE SAME

(71) Applicant: C-Motive Technologies, Inc., Middleton, WI (US)

(72) Inventors: Graham T. Reitz, Middleton, WI (US); William D. Butrymowicz, Middleton, WI (US); Justin K Reed, Madison, WI (US); Daniel C. Ludois, Middleton, WI (US)

(73) Assignee: C-Motive Technologies, Inc., Middleton, WI (US)

( * ) Notice: Subject to any disclaimer, the term of this patent is extended or adjusted under 35 U.S.C. 154(b) by 777 days.

This patent is subject to a terminal disclaimer.

(21) Appl. No.: 18/117,239

(22) Filed: Mar. 3, 2023

(65) Prior Publication Data

US 2023/0223869 A1 Jul. 13, 2023

Related U.S. Application Data

(63) Continuation of application No. 17/461,087, filed on Aug. 30, 2021, now Pat. No. 11,601,069, which is a (Continued)

(51) Int. Cl.

| | |
|---|---|
| ***H02N 1/00*** | (2006.01) |
| ***C07C 69/00*** | (2006.01) |
| ***C08J 3/09*** | (2006.01) |

(52) U.S. Cl.

CPC ............ *H02N 1/002* (2013.01); *H02N 1/004* (2013.01); *C07C 69/00* (2013.01); *C08J 3/095* (2013.01)

(58) Field of Classification Search

CPC .......... H02N 1/00; H02N 1/002; H02N 1/004; H02N 1/006

See application file for complete search history.

(56) References Cited

U.S. PATENT DOCUMENTS

| | | | |
|---|---|---|---|
| 3,094,653 | A | 6/1963 | Le May et al. |
| 3,400,282 | A | 9/1968 | Felici |

(Continued)

FOREIGN PATENT DOCUMENTS

| | | |
|---|---|---|
| DE | 40 35 750 | 6/1991 |
| JP | 07-298647 | 11/1995 |

(Continued)

OTHER PUBLICATIONS

Buysch, "Ullman's Encyclopedia Of Industrial Chemistry", 2012, vol. 7, pp. 45-71 (Year: 2012).

(Continued)

*Primary Examiner* — Eric Johnson

(74) *Attorney, Agent, or Firm* — Foley & Lardner LLP

(57) ABSTRACT

An electrostatic machine includes a drive electrode and a stator electrode. The drive electrode and the stator electrode are separated by a gap and form a capacitor. The drive electrode is configured to move with respect to the stator electrode. The electrostatic machine further includes a housing configured to enclose the drive electrode and the stator electrode. The stator electrode is fixed to the housing. The electrostatic machine also includes a dielectric fluid that fills a void defined by the housing, the drive electrode, and the stator electrode. The dielectric fluid includes an ester.

17 Claims, 23 Drawing Sheets

Related U.S. Application Data continuation of application No. 16/347,975, filed as application No. PCT/US2017/060347 on Nov. 7, 2017, now Pat. No. 11,114,951.

(60) Provisional application No. 62/419,128, filed on Nov. 8, 2016.

(56) References Cited

U.S. PATENT DOCUMENTS

| | | | | |
|---|---|---|---|---|
| 3,433,981 | A | 3/1969 | Bollee | |
| 4,276,184 | A * | 6/1981 | Mandelcorn | H01G 4/221 252/579 |
| 6,353,276 | B1 | 3/2002 | Gendron | |
| 7,834,513 | B2 | 11/2010 | Post | |
| 8,264,121 | B2 | 9/2012 | Post | |
| 8,278,797 | B2 | 10/2012 | Sashida | |
| 8,643,249 | B2 | 2/2014 | Post | |
| 8,779,647 | B2 | 7/2014 | Sashida | |
| 9,614,462 | B2 | 4/2017 | Post | |
| 9,748,867 | B2 | 8/2017 | Hawes et al. | |
| 9,806,639 | B2 | 10/2017 | Chen et al. | |
| 9,998,052 | B2 | 6/2018 | Shimada et al. | |
| 10,027,205 | B2 | 7/2018 | Boughtwood | |
| 10,056,848 | B2 | 8/2018 | Johnson | |
| 10,148,198 | B2 | 12/2018 | Johnson | |
| 10,504,656 | B2 | 12/2019 | Grubic et al. | |
| 10,666,145 | B2 | 5/2020 | Chaput et al. | |
| 10,720,841 | B2 | 7/2020 | Chaput et al. | |
| 10,778,119 | B2 | 9/2020 | Goodson et al. | |
| 10,931,199 | B2 | 2/2021 | Chaput et al. | |
| 10,958,191 | B2 | 3/2021 | Kratchman et al. | |
| 11,374,496 | B2 | 6/2022 | Chaput et al. | |
| 11,777,422 | B2 | 10/2023 | Kedzierski | |
| 11,863,086 | B2 | 1/2024 | Kratchman et al. | |
| 12,119,760 | B1 | 10/2024 | Kratchman et al. | |
| 2005/0006980 | A1 | 1/2005 | Horst | |
| 2005/0072964 | A1 | 4/2005 | Rapp et al. | |
| 2006/0214535 | A1 | 9/2006 | Salmon | |
| 2010/0237629 | A1 | 9/2010 | Gray | |
| 2012/0282120 | A1 | 11/2012 | Krahn et al. | |
| 2014/0252914 | A1 | 9/2014 | Post | |
| 2015/0134109 | A1 | 5/2015 | Zhou et al. | |
| 2016/0099663 | A1 | 4/2016 | Petrowsky et al. | |
| 2024/0372486 | A1 | 11/2024 | Ward | |

FOREIGN PATENT DOCUMENTS

| | | |
|---|---|---|
| JP | H958801 | 3/1997 |
| JP | 2007-077312 | 3/2007 |
| JP | 2008-017784 | 1/2008 |
| WO | WO-2012/102915 A1 | 8/2012 |
| WO | WO-2016/048850 | 3/2016 |
| WO | WO-2016/052338 | 4/2016 |
| WO | WO-2016/057333 | 4/2016 |
| WO | WO-2024/073833 A1 | 4/2024 |
| WO | WO-2024/168335 A1 | 8/2024 |
| WO | WO-2024/228742 A1 | 11/2024 |

OTHER PUBLICATIONS

Cargill, "Fr3 Fluid Technical Details Webpage" (Year: 2021).

Ge et al., "Evaluation Of Dielectric Fluids For Macro-Scale Electrostatic Actuators And Machinery", IEEE, 2014, pp. 1457-1464 (Year: 2014).

International Search Report and Written Opinion on International Application No. PCT/US2017/060347 dated Feb. 21, 2018. 14 pages.

* cited by examiner

1100

1150

ELECTROSTATIC MACHINE SYSTEM HAVING A DIELECTRIC FLUID AND A METHOD OF OPERATION OF THE SAME

CROSS-REFERENCE TO RELATED APPLICATIONS

The present application is a continuation of U.S. patent application Ser. No. 17/461,087, filed on Aug. 30, 2021, which is a continuation of U.S. patent application Ser. No. 16/347,975, filed on May 7, 2019, and which claims priority under 35 U.S.C. § 371 to International Patent Application No. PCT/US2017/060347, filed on Nov. 7, 2017 which claims the benefit of priority to U.S. Provisional Patent Application No. 62/419,128, filed on Nov. 8, 2016, all of which are incorporated herein by reference in their entireties.

STATEMENT OF GOVERNMENT RIGHTS

The present disclosure was made with government support under IIP 1534684 awarded by the National Science Foundation. The government has certain rights in the invention.

FIELD

The present technology generally relates to electrostatic rotating machines and a fill fluid for such machines. More particularly, the technology relates to machines such as motors and generators that have capacitance plates separated by a fluid, such as a dielectric fluid.

SUMMARY

An illustrative electrostatic machine includes a drive electrode and a stator electrode. The drive electrode and the stator electrode are separated by a gap and form a capacitor. The drive electrode is configured to move with respect to the stator electrode. The electrostatic machine further includes a housing configured to enclose the drive electrode and the stator electrode. The stator electrode is fixed to the housing. The electrostatic machine also includes a dielectric fluid that fills a void defined by the housing, the drive electrode, and the stator electrode. The dielectric fluid includes an ester.

An illustrative electrostatic machine includes a shaft configured to rotate about an axis. The machine also includes a rotor electrode and a stator electrode separated by a gap and forming a capacitor. The rotor electrode is fixed to the shaft. The machine further includes a housing configured to enclose the rotor electrode, the stator electrode, and a portion of the shaft. The stator electrode is fixed to the housing. The machine also includes a dielectric fluid that fills a void defined by the housing, the rotor electrode, and the stator electrode. The dielectric fluid includes an ester.

In some embodiments, the ester is a compound of formula RC(O)O—R', wherein R and R' are individually a substituted or unsubstituted alkyl or alkenyl group. In some embodiments, R and R' are individually a substituted or unsubstituted $C_1$-$C_{30}$ alkyl or alkenyl group. In some embodiments, R and R' are individually a substituted or unsubstituted $C_1$-$C_{24}$ alkyl or alkenyl group. In some embodiments, R and R' are individually a substituted or unsubstituted $C_1$-$C_{12}$ alkyl or alkenyl group. In some embodiments, R may be a substituted or unsubstituted $C_5$-$C_{10}$ alkyl group or a substituted or unsubstituted $C_5$-$C_{12}$ alkenyl group; and R' may be a substituted or unsubstituted $C_1$-$C_3$ alkyl group; or R' may be a substituted or unsubstituted $C_5$-$C_{10}$ alkyl group or a substituted or unsubstituted $C_5$-$C_{12}$ alkenyl group; and R may be a substituted or unsubstituted $C_1$-$C_3$ alkyl group. In some embodiments, the ester may be selected from the group consisting of:

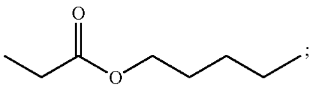

pentyl propionoate

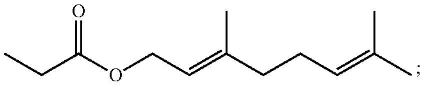

geranyl propionoate

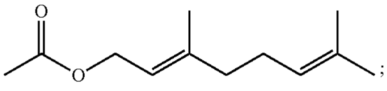

geranyl acetate

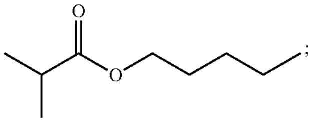

pentyl isobutyrate

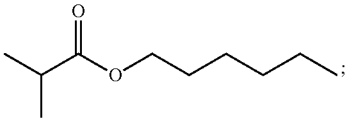

hexyl isobutyrate

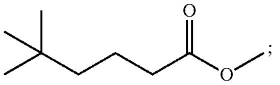

methyl 5,5-dimethylhexanoate

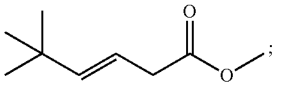

methyl (E)-5,5-dimethylhexanoate-3-enoate

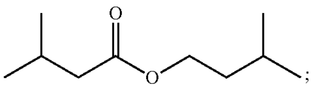

isoamyl isovalerate and combinations of two or more thereof.

In other embodiments, the ester is malonate of formula RO(C(O)$CH_R$"C(O)OR', wherein R, R', and R" are individually a substituted or unsubstituted alkyl or alkenyl group. In some embodiments, R, R', and R" are individually a substituted or unsubstituted $C_1$-$C_{30}$ alkyl or alkenyl group. In some embodiments, R, R', and R" are individually a substituted or unsubstituted $C_1$-$C_{24}$ alkyl or alkenyl group. In some embodiments, R, R', and R" are individually a substituted or unsubstituted $C_1$-$C_{12}$ alkyl or alkenyl group. In some embodiments, R, R', and R may be a substituted or unsubstituted $C_1$-$C_3$ alkyl group. In some embodiments, the ester may be diethyl malonate, diethylethyl malonate, methylethyl malonate, ethylpropyl malonate, dipropyl malonate, and the like, or a mixture of any two or more thereof.

In any of the above embodiments, the ester may include a mixture of any of the above esters.

In some embodiments, the dielectric fluid further includes a carbonate moiety. In some embodiments, the dielectric fluid further includes a nitrile substituted heteroaromatic solvent. In some embodiments, the dielectric fluid further includes 2-pyridinecarbonitrile. In some embodiments, the dielectric fluid further includes about 10 wt % 2-pyridinecarbonitrile and about 90 wt % propylene carbonate. In some embodiments, the dielectric fluid further includes a cyclic structure, and a moiety represented as —OC(O)N—. In some embodiments, the dielectric fluid further includes 3-methyl-2-oxazolidinone, 3-ethyl-2-oxazolidinone, or 3-methyl-1,3-oxazinan-2-one.

In some embodiments, the dielectric fluid further includes a fluorinated acyclic hydrocarbon. In some embodiments, the dielectric fluid further includes $C_5H_2F_{10}$. In some embodiments, the dielectric fluid further includes a sulfonyl group. In some embodiments, the dielectric fluid further includes dimethyl sulfone, sulfolane, or a mixture thereof. In some embodiments, the dielectric fluid further includes ethylene carbonate, dimethyl carbonate, diethyl carbonate, ethylmethyl carbonate, dipropyl carbonate, propylene carbonate, methyl butyrate, γ-butyrolactone, N-methylpyrrolidinone, vinylene carbonate, dioxolane, δ-butyrolactone, diethyl ether, or a mixture of any two or more thereof. In some embodiments, the dielectric fluid further includes propylene carbonate having a purity of greater than 99%.

In some embodiments, the rotor electrode and the stator electrode each comprise a passivation layer formed using a second dielectric in the gap between the rotor electrode and the stator electrode, and wherein the second dielectric fluid includes less than 99 wt % propylene carbonate. In an example embodiment, a direct current voltage is applied across the rotor electrode and the stator electrode to form the passivation layer.

In some embodiments, the machine further includes a current sourced inverter configured to convert direct current power into alternating current power via a plurality of switches. The current sourced inverter is configured to provide the alternating current power across the rotor electrode and the stator electrode. No passive electrical components are electrically connected between the rotor electrode, the stator electrode, and the plurality of switches.

In some embodiments, the machine further includes a voltage sourced inverter configured to convert direct current power into alternating current power via a plurality of switches. A plurality of inductors is electrically connected between the rotor electrode, the stator electrode, and the plurality of switches.

In some embodiments, the rotor electrode comprises a rotor plate. The stator electrode includes a stator plate, and the rotor plate and the stator plate are parallel. In an illustrative embodiment, the rotor plate includes a plurality of teeth around a periphery of the rotor plate. The stator plate includes an annulus with a plurality of teeth extending from an inside circumference of the annulus. The teeth of the rotor plate and the teeth of the stator plate form the capacitor. In some embodiments, the housing includes at least one of polypropylene, acetal, chemical resistant acetal, ultra-high-molecular-weight (UHMW) polyethylene, polyetherimide (e.g., Ultem® produced by Aetna Plastics), and polytetrafluoroethylene (PTFE). In some embodiments, the housing includes at least one of fluoropolymer elastomer (e.g., Viton® produced by The Chemours Company), high-density polyethylene (HDPE), acetal, fluoropolymer elastomer (FEP) with a silicone core, polyurethane, and a copolymer of tetrafluoroethylene/propylene (e.g., Aflas® produced by Asahi Glass Co., Ltd.). In alternative embodiments, the housing can be made of any suitable material that is compatible with esters.

In some embodiments, the rotor electrode comprises a rotor plate. The stator electrode includes a stator plate, and the rotor plate and the stator plate are parallel. In an illustrative embodiment, the rotor plate includes a plurality of veins extending from an inside circumference to an annulus at an outer circumference. The stator plate includes a plurality of veins extending from an annulus at an outer circumference to an annulus at an inner circumference. The annuli and the spokes of each of the rotor plate and the stator plate form the capacitor. In some embodiments, the housing includes at least one of polypropylene, acetal, ultra-high-molecular-weight (UHMW) polyethylene, polyetherimide, and polytetrafluoroethylene (PTFE). In some embodiments, the housing includes at least one of fluoropolymer elastomer (e.g., Viton® produced by The Chemours Company), high-density polyethylene (HDPE), acetal, fluoropolymer elastomer (FEP) with a silicone core, polyurethane, and a copolymer of tetrafluoroethylene/propylene (e.g., Aflas® produced by Asahi Glass Co., Ltd.). In some embodiments that employ acetal, it may be chemical resistant acetal. In alternative embodiments, the housing can be made of any suitable material that is compatible with esters.

An illustrative electrostatic machine includes a shaft that is configured to rotate about an axis, a rotor electrode, and a stator electrode. The rotor electrode and the stator electrode are separated by a gap and form a capacitor. The rotor electrode is fixed to the shaft. In an alternative embodiment, the shaft can be a hollow shaft. The electrostatic machine can also include a housing that is configured to enclose the rotor electrode, the stator electrode, and at least a portion of the shaft. The stator electrode is fixed to the housing. A dielectric fluid fills a void defined by the housing, the rotor electrode, and the stator electrode. The dielectric fluid comprises at least one of an acyclic structure or a cyclic structure.

In some embodiments, the rotor electrode comprises a rotor plate with pegs oriented in the axial direction. The stator electrode includes a stator plate with pegs oriented in the axial direction, and the rotor plate and the stator plate are parallel. In an illustrative embodiment, the stator and rotor pegs are interleaved and move past each other without touching when the rotor rotates. In some embodiments, the housing includes at least one of polypropylene, acetal, ultra-high-molecular-weight (UHMW) polyethylene, polyetherimide), and polytetrafluoroethylene (PTFE). In some embodiments, the housing includes at least one of fluorinate viton (flouroelastomer), high-density polyethylene (HDPE), acetal, fluoropolymer elastomer (FEP) with a silicone core, polyurethane, and AFLAS. In some embodiments that employ acetal, it may be chemical resistant acetal. In alternative embodiments, the housing can be made of any suitable material that is compatible with esters.

In some embodiments, the dielectric fluid is a carbonate (i.e. —OC(O)O—). In some embodiments, the dielectric fluid includes an aromatic structure in which a nitrogen atom is present at a first position in a ring of the aromatic structure and at least one nitrile (CN) group is a substituent at a second position. In some embodiments, the dielectric fluid includes 2-pyridinecarbonitrile.

In some embodiments, the dielectric fluid comprises a cyclic structure and includes a chemical functional group represented as —OC(O)N—. In some embodiments, the dielectric fluid includes 3-methyl-2-oxazolidinone, 3-ethyl-2-oxazolidinone, 3-methyl-1,3-oxazinan-2-one, or a mixture of any two or more thereof. In some embodiments, the dielectric fluid includes an acyclic, fluorinated hydrocarbon. In some embodiments, the dielectric fluid includes $C_5H_2F_{10}$.

In some embodiments, the dielectric fluid is an organic compound having a sulfonyl moiety (—$S(O)_2$—). In some embodiments, the dielectric fluid includes dimethyl sulfone, sulfolane, or a mixture thereof.

In some embodiments, the dielectric fluid includes ethylene carbonate, dimethyl carbonate, diethyl carbonate, ethylmethyl carbonate, dipropyl carbonate, propylene carbonate, methyl butyrate, γ-butyrolactone, N-methylpyrrolidinone, vinylene carbonate, dioxolane, 6-butyrolactone, or diethyl ether. In some embodiments, the dielectric fluid includes propylene carbonate having a purity of greater than 99%. In some embodiments, the rotor electrode and the stator electrode each comprise a passivation layer formed using a second dielectric in the gap between the rotor electrode and the stator electrode. The second dielectric fluid comprises less than 99 wt % propylene carbonate. In some embodiments, the second dielectric fluid includes 93.8 vol % propylene carbonate, 6 vol % ethylene sulfite, and 0.2 vol % water. In some embodiments, a voltage is applied across the capacitor, and wherein the dielectric fluid forms a passivation layer on a surface of the rotor electrode and on a surface of the stator electrode.

In some embodiments, the electrostatic machine can further include a current sourced inverter that is configured to convert direct current power into alternating current power via a plurality of switches. The current sourced inverter is configured to provide the alternating current power across the rotor electrode and the stator electrode. No passive electrical components are electrically connected between the rotor electrode, the stator electrode, and the plurality of switches.

In some embodiments, the electrostatic machine can further include a voltage sourced inverter that is configured to convert direct current power into alternating current power via a plurality of switches. A plurality of inductors is electrically connected between the rotor electrode, the stator electrode, and the plurality of switches.

In some embodiments, the rotor electrode comprises a rotor plate, the stator electrode comprises a stator plate, and the rotor plate and the stator plate are parallel. The rotor plate comprises a plurality of teeth around a periphery of the rotor plate. The stator plate comprises an annulus with a plurality of teeth extending from an inside circumference of the annulus. The teeth of the rotor plate and the teeth of the stator plate form the capacitor. In some embodiments, the housing comprises at least one of polypropylene, acetal, chemical resistant acetal, ultra-high-molecular-weight (UHMW) polyethylene, polyetherimide, and polytetrafluoroethylene (PTFE). In some embodiments, the housing includes at least one of fluoropolymer elastomer (e.g., Viton® produced by The Chemours Company), high-density polyethylene (HDPE), acetal, fluoropolymer elastomer (FEP) with a silicone core, polyurethane, and a copolymer of tetrafluoroethylene/propylene (e.g., Aflas® produced by Asahi Glass Co., Ltd.). In alternative embodiments, the housing can be made of any suitable material that is compatible with esters.

The foregoing summary is illustrative only and is not intended to be in any way limiting. In addition to the illustrative aspects, embodiments, and features described above, further aspects, embodiments, and features will become apparent by reference to the following drawings and the detailed description.

Figures 1A, 1B:
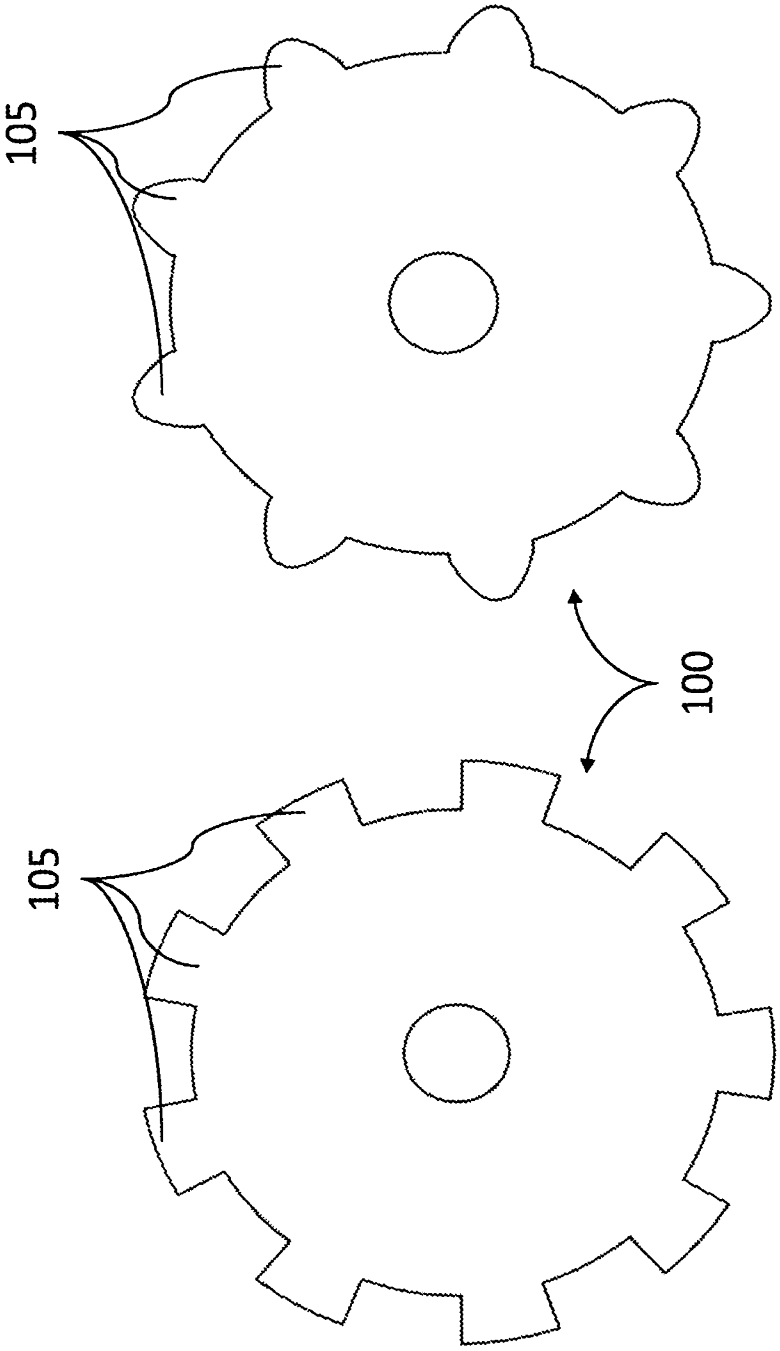
FIGS. 1A-1C illustrate cross-sectional views of some shapes of a rotor disk or plate in accordance with illustrative embodiments.
Figure 1D:
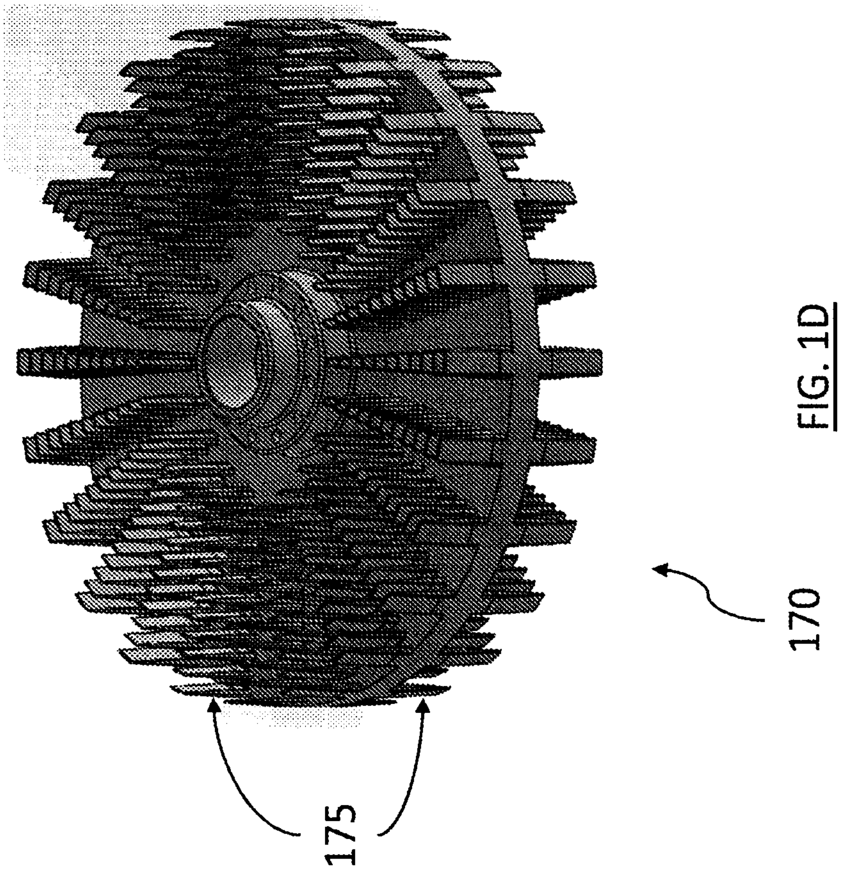
FIG. 1D is a three-dimensional view of a rotor disk or plate with pegs in accordance with an illustrative embodiment.

The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

Electrostatic machinery include electric motors and generators that convert power between mechanical (e.g., kinetic) and electrical forms using electric field torque mechanisms. In general, electrostatic machines use capacitive principles (as opposed to inductive principles used in induction, permanent magnet, and reluctance machines). In some embodiments, electrostatic machines can use circular plates located in close proximity to one another to create a capacitance between the plates. In some embodiments, the plates can alternate between rotor plates and stator plates. Rotor plates can be plates that rotate with a shaft of the motor and/or generator and can be analogous to an armature of an induction or reluctance motor. Stator plates can remain stationary with respect to a housing or enclosure of the motor and/or generator. The housing or enclosure made be made of any material that is appropriate to the application and is compatible with the fluids used therein. For example, the material may be a metal, a polymer, a ceramic, or a glass. In some embodiments, the enclosure is made from aluminum or stainless steel.

In general, energy storage systems (e.g., capacitors) can naturally arrange themselves to be in a minimal energy state. In the case of variable capacitance machines (and other electrostatic machines), surfaces affixed to a shaft (e.g., rotor plates) can form a capacitance with surfaces affixed to a housing (e.g., stator plates). When voltage is applied across rotor plates and the stator plates, an electric field develops between the rotor plates and the stator plates and can exert a force (e.g., torque) on the surfaces of the rotor plates and the stator plates in a direction that will align the rotor plates and the stator plates in a position with a minimal energy state. The rotor plates and the stator plates are electrodes that form a capacitor.

Some electrostatic machines can produce a large electric field across a pair of electrodes (e.g., stator plates and rotor plates) to generate sufficient torque and force for practical applications. Air has a low breakdown voltage (e.g., is prone to arcing). Thus, in some embodiments, a dielectric fluid can be located between the electrodes (e.g., stator plates and rotor plates) and a high electric field can be maintained without arcing between the electrodes.

Torque and force generation in an electrostatic machine can be directly related to the normal and shear forces between the electrodes. The electrostatic normal force density F between the electrodes can be estimated using Coulomb's law:

$$F=(\tfrac{1}{2})\varepsilon_0\varepsilon E^2$$

where $\varepsilon_0$ is the vacuum permittivity of the medium between the electrodes in farads per meter (F/m), $\varepsilon$ is the static permittivity of the medium between the electrodes, and E is the electric field in volts per meter (V/m). The force density can be optimized by using a medium between the electrodes that has a high permittivity and by applying a large electric field across the electrodes without arcing between the electrodes. In some embodiments, the medium can be in a liquid state. In most instances, liquids can have a higher relative permittivity than gases. Other considerations can be taken into account when choosing a fill medium. For example, the ionic conductivity of the medium can be low. Ionic contaminants can facilitate electron transport between the electrodes, resulting in premature dielectric breakdown and, thus, inhibiting application of a high electric field. Liquid viscosity can be low thereby minimizing drag on moving parts. In some instances, a fluid with high permittivity and low conductivity, which can be located between rotor plates and stator plates, can be generally referred to as a dielectric fluid. However, in other instances, a fluid with low relative permittivity can be used. For example, in some embodiments, acyclic carbonates and/or ethers can be used, which may have a low relative permittivity but may have other desirable characteristics. In other embodiments, esters may be used. The esters may have high or low relative permittivity (e.g., compared to acyclic carbonates).

Electrostatic machines may be divided into six categories: electrostatic induction machines, variable capacitance/elastance machines, synchronous electrostatic machines, direct current (DC) electrostatic machines, electrostatic hysteresis synchronous machines, and corona machines. In some instances, a particular machine may fall into one or more of the categories. Such categories are not exclusive, and additional categories may exist. The use of such categories is used for explanatory purposes only, and is not meant to be limiting. The following descriptions of the categories explain the general, underlying principles used in the machines of each category.

Electrostatic induction machines can use electrodes on a stator to produce a traveling potential wave. The potential wave can induce a charge distribution on a rotor adjacent to the stator. The rotor surface can be continuous and, in at least some instances, does not exhibit capacitive saliency. When the stator and the rotor have a net velocity between them (e.g., the stator and the rotor move relative to one another), a tangential component of the electrical field in a gap between the stator and the rotor can exist in the gap. The tangential component can result in a coulomb force on the rotor charge. The relative velocity between the stator and rotor can be referred to as the slip speed. In some aspects, electrostatic induction machines can be considered to be analogous to magnetic induction machines that use a version of slip.

Variable capacitance machines can be referred to as elastance machines. Variable capacitance machines can minimize elastance (or maximize capacitance) to create torque. When a voltage is applied across stator electrodes and rotor electrodes, the rotor electrodes can experience a torque in a direction to align the rotor to be in a minimum energy state with respect to the stator. The torque can be proportional to the change in capacitance per unit angle (e.g., $dC/d\theta$). Variable capacitance machines can be designed to maximize the change in capacitance over a rotational angle. The manner in which the capacitance varies with angle may be synchronous (e.g., sinusoidal) or switched (e.g., trapezoidal). In some aspects, variable capacitance machines can be considered to be analogous to magnetism based variable reluctance machines.

Synchronous electrostatic machines can have a rotor with a fixed DC charge distribution across the rotor. The DC charge distribution can provide a DC electric flux field in the frame of the rotor. The DC field can rotate with the rotor. Electrodes of the stator can produce an alternating current (AC) charge and corresponding electric field distribution that follows the rotor as the rotor rotates. The rotor flux and the stator flux can travel at the same speed (e.g., a synchronous speed). Although the rotor flux and the stator flux travel at the same speed, the angle between the rotor flux vectors and the stator flux vectors can determine torque by varying the shear in the gap. In some embodiments, the rotor flux may be produced with a permanent electret or may be separately excited using a power supply connected through a rotating shaft power coupling (e.g. brushes and slip rings). In some aspects, synchronous electrostatic machines can be considered to be analogous to magnetic synchronous machines.

The underlying principles of direct current (DC) electrostatic machines are similar to those of synchronous electrostatic machines. However, in DC electrostatic machines, the roles of the stator and rotor are reversed from the roles of the stator and the rotor in synchronous electrostatic machines. Stator electrodes can be excited using DC power, thereby creating a static field. Charge on the rotor, however, can be commutated mechanically. As the rotor spins, charge is commutated by a brushed commutator or a non-brushed commutator such that the charge is aligned with the stator excitation, thereby producing average torque. In some aspects, DC electrostatic machines can be considered to be analogous to magnetic DC motors.

Electrostatic hysteresis synchronous machines are analogous to traditional synchronous machines in that rotor and stator flux interact to make torque. However, in electrostatic hysteresis synchronous machines, ferroelectric materials with an electrostatic hysteresis curve of an electric field versus displacement (e.g., an E-D hysteresis curve) can coat the rotor surface. An E-D hysteresis curve can be a function of the electric displacement D for an applied electric field E. In some aspects, an E-D curve for ferroelectric materials can be analogous to a B-H curve for ferromagnetic materials. The slope of an E-D curve for a material can represent the permittivity of the material at different electric field strengths. The ferroelectric material can be polarized during operation and dragged along with the stator flux wave at synchronous speed. In some aspects, electrostatic hysteresis synchronous machines can be considered to be analogous to magnetic hysteresis synchronous motors.

Corona machines are different than machines of the other five categories explained above in that the operating principle is electro hydrodynamic flow rather than creating electric shear force via normal and/or tangential fields. Charged particles can be accelerated to form an ionic "wind." The mechanical interaction of the accelerated particles with rotor and stator structures can create torque. Corona machines can incur high electrical losses at macro scales and, therefore, may not be suitable for many applications.

FIGS. 1-8 illustrate various aspects of a variable capacitance machine. A variable capacitance machine can include a shaft, a frame and/or housing, rotor plates, stator plates, and a dielectric fluid that fills the space inside the housing not otherwise occupied by the other parts. The dielectric fluid will be discussed in greater detail below. Although FIGS. 1-8 illustrate embodiments in which rotor electrodes rotate within stator electrodes (e.g., the rotor electrodes are fixed to a central shaft with stator electrodes encircling the central shaft), any suitable capacitance machine may be used. For example, in some embodiments an external rotor motor can be used. In such embodiments, stator electrodes can be fixed along an axis, and rotor electrodes can surround the stator electrodes. That is, the rotor electrodes can rotate around the stator electrodes.

Figure 1C:
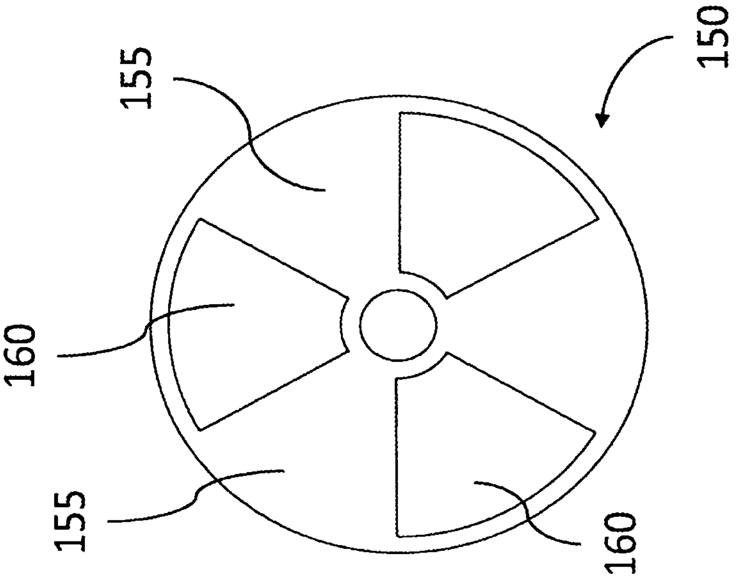

FIGS. 1A-1C illustrate cross-sectional views of some shapes of a rotor disk or plate in accordance with illustrative embodiments. The rotor plates 100 illustrated in FIGS. 1A and 1B have teeth 105 around an outside circumference of the plates. The rotor plate 150 of FIG. 1C has conductive portions 155 and non-conductive portions 160. For example, the rotor plate 150 may be conductive, and non-conductive portions 160 can be cut outs of the rotor plate 150. The rotor plate 170 of FIG. 1D includes multiple pegs 175. In the embodiment shown in FIG. 1D, the rotor plate 170 has pegs 175 on each side of the rotor plate 170. In alternative embodiments, the rotor plate 170 may have pegs 175 on one side.

Figures 2A, 2B:
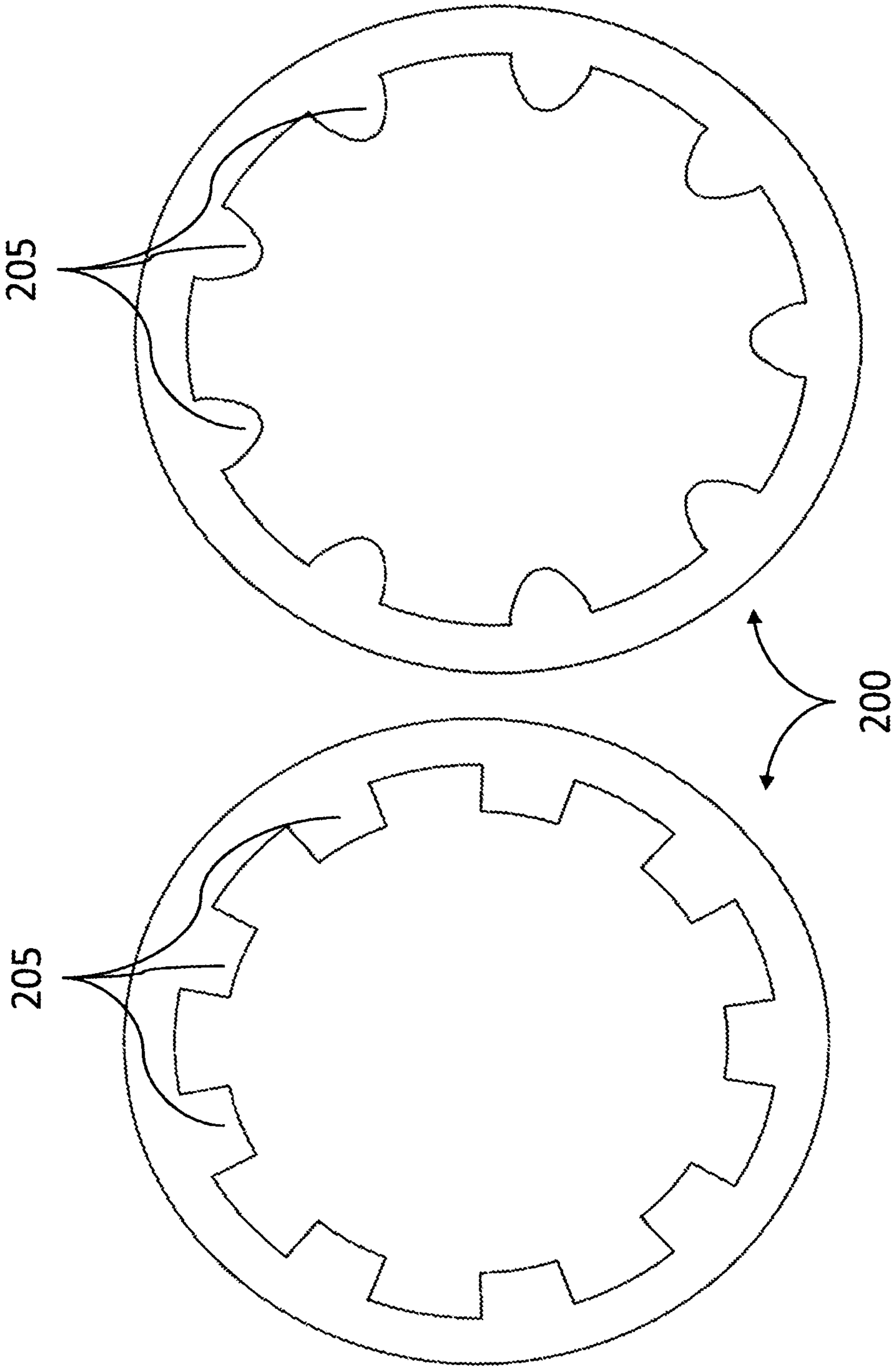
FIGS. 2A-2C illustrate cross-sectional views of some shapes of a stator ring/plate in accordance with illustrative embodiments.
Figure 2C:
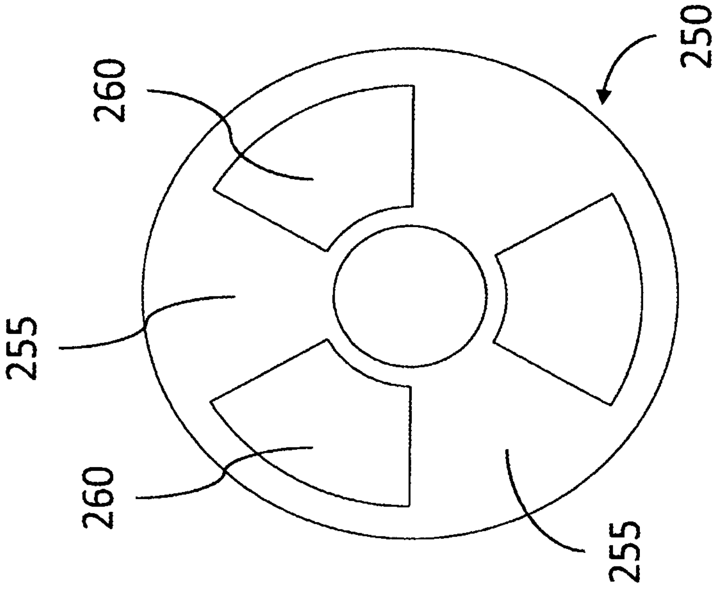
Figure 2D:
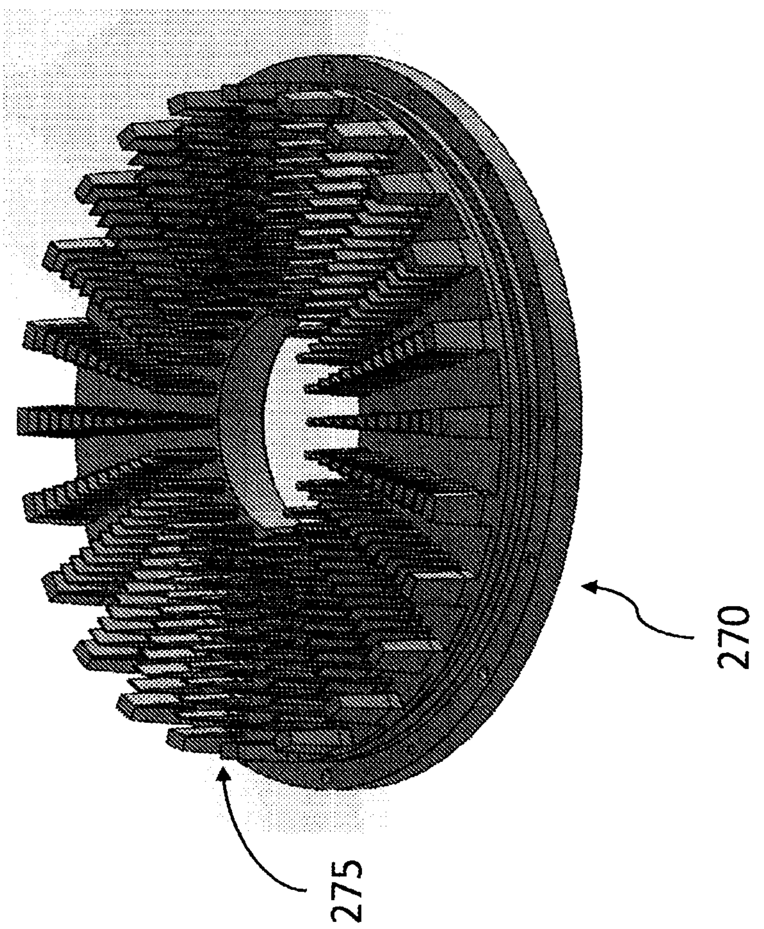
FIG. 2D is a three-dimensional view of a stator disk or plate with pegs in accordance with an illustrative embodiment.

FIGS. 2A-2C illustrate cross-sectional views of some shapes of a stator ring/plate in accordance with illustrative embodiments. The stator plates 200 can have teeth 205 along an inside circumference of the stator plates 200. In an illustrative embodiment, the rotor plate 100 illustrated in FIG. 1A can be used with the stator plate 200 illustrated in FIG. 2A. In an alternative embodiment, the rotor plate 100 illustrated in FIG. 2B can be used with the stator plate 200 illustrated in FIG. 2B. The stator plate 250 of FIG. 2C has conductive portions 255 and non-conductive portions 260. For example, the stator plate 250 may be conductive, and non-conductive portions 260 can be cut outs of the stator plate 250. The stator plate 270 of FIG. 2D includes multiple pegs 275. In the embodiment shown in FIG. 2D, the stator plate 270 has pegs 275 on one side of the stator plate 270. In alternative embodiments, the stator plate 270 may have pegs 275 on both sides. In an illustrative embodiment, the pegs 175 of the rotor plate 170 and the pegs 275 of one side of the stator plate 270 pass along one another as the rotor plate 170 rotates with respect to the stator plate 270.

In other embodiments, a combination of rotor plate and stator plate shapes can be used. Further, the rotor plate and stator plate shapes illustrated in FIGS. 1A-1D and 2A-2D illustrate some examples of shapes that can be used. In alternative embodiments, any other suitable shape can be used. That is, the specific shapes of electrodes described herein are meant to be illustrative only. As described in greater detail below, the dielectric fluid disclosed can be used in any suitable electrostatic machine regardless of electrode shape or style. Furthermore, although electromagnetic motors are described herein, the dielectric fluid can be used in any type of electrostatic machine such as actuators, linear motors, etc. The use of the dielectric fluid in electrostatic machines is not meant to be limited to the styles or features specifically described herein.

In some embodiments, the teeth 105 of the rotor plate 100 can overlap with teeth 205 of the stator plate 200 when assembled. The teeth 105 and the teeth 205 may also be referred to as "electrodes." FIG. 3A is a diagram illustrating the capacitive relationship between a rotor and stators in accordance with an illustrative embodiment. In alternative embodiments, additional, fewer, and/or different elements can be used. As shown in FIG. 3A, stator teeth 205 can be located in a plane parallel to the plane of rotor teeth 105. The stator teeth 205 can be positively charged and the rotor teeth 105 can be negatively charged. In alternative embodiments, the rotor teeth 105 can be positively charged and the stator teeth 205 can be negatively charged. In yet other embodiments, the rotor teeth 105 and the stator teeth 205 can alternate polarities over time.

Figure 3B:
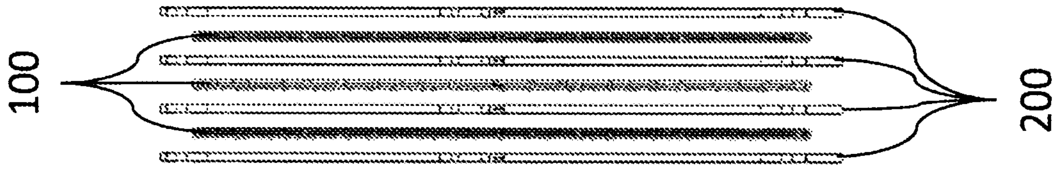
FIG. 3B illustrates the positional relation of rotors and stators in accordance with an illustrative embodiment.
Figure 3A:
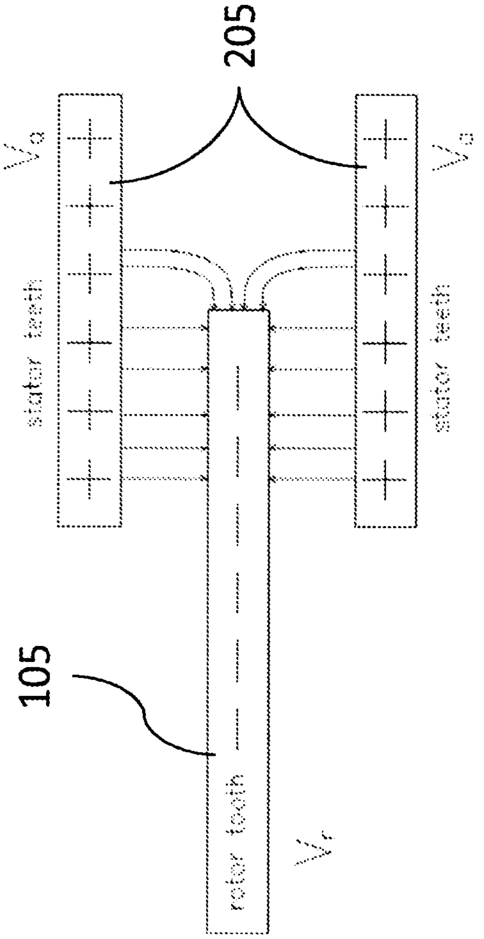
FIG. 3A is a diagram illustrating the capacitive relationship between a rotor and stators in accordance with an illustrative embodiment.
Figure 3C:
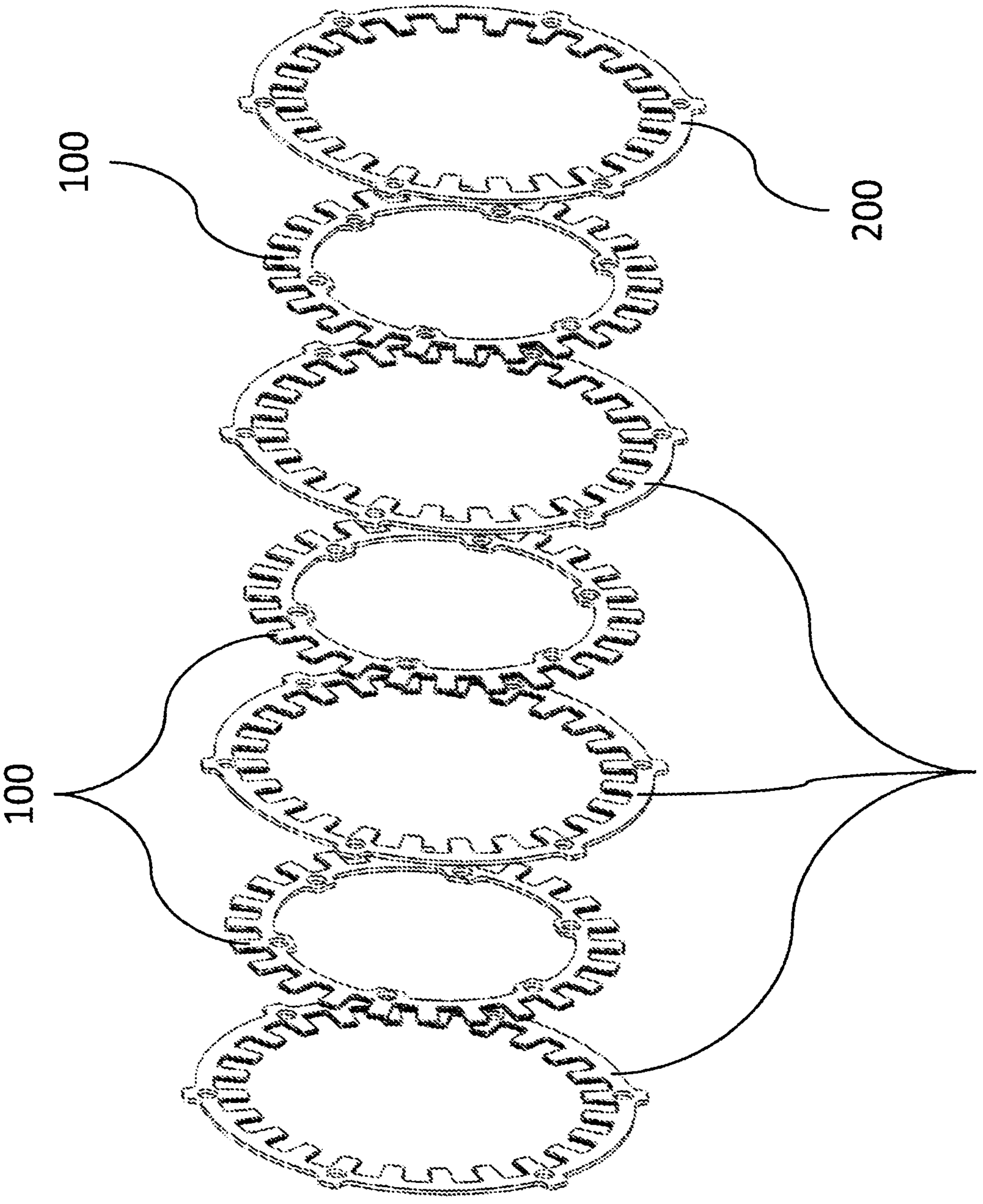
FIG. 3C is an illustration of an exploded view of a configuration of stators and rotors in accordance with an illustrative embodiment.

FIG. 3B illustrates the positional relation of rotors and stators in accordance with an illustrative embodiment. FIG. 3C is an illustration of an exploded view of a configuration of stators and rotors in accordance with an illustrative embodiment. In alternative embodiments, additional, fewer, and/or different elements can be used. A plurality of rotor plates 100 and stator plates 200 can be alternately stacked together in a motor. In some embodiments, the number of rotor plates 100 and corresponding stator plates 200 can determine, at least in part, the amount of torque and/or power produced by the motor.

Figure 3D:
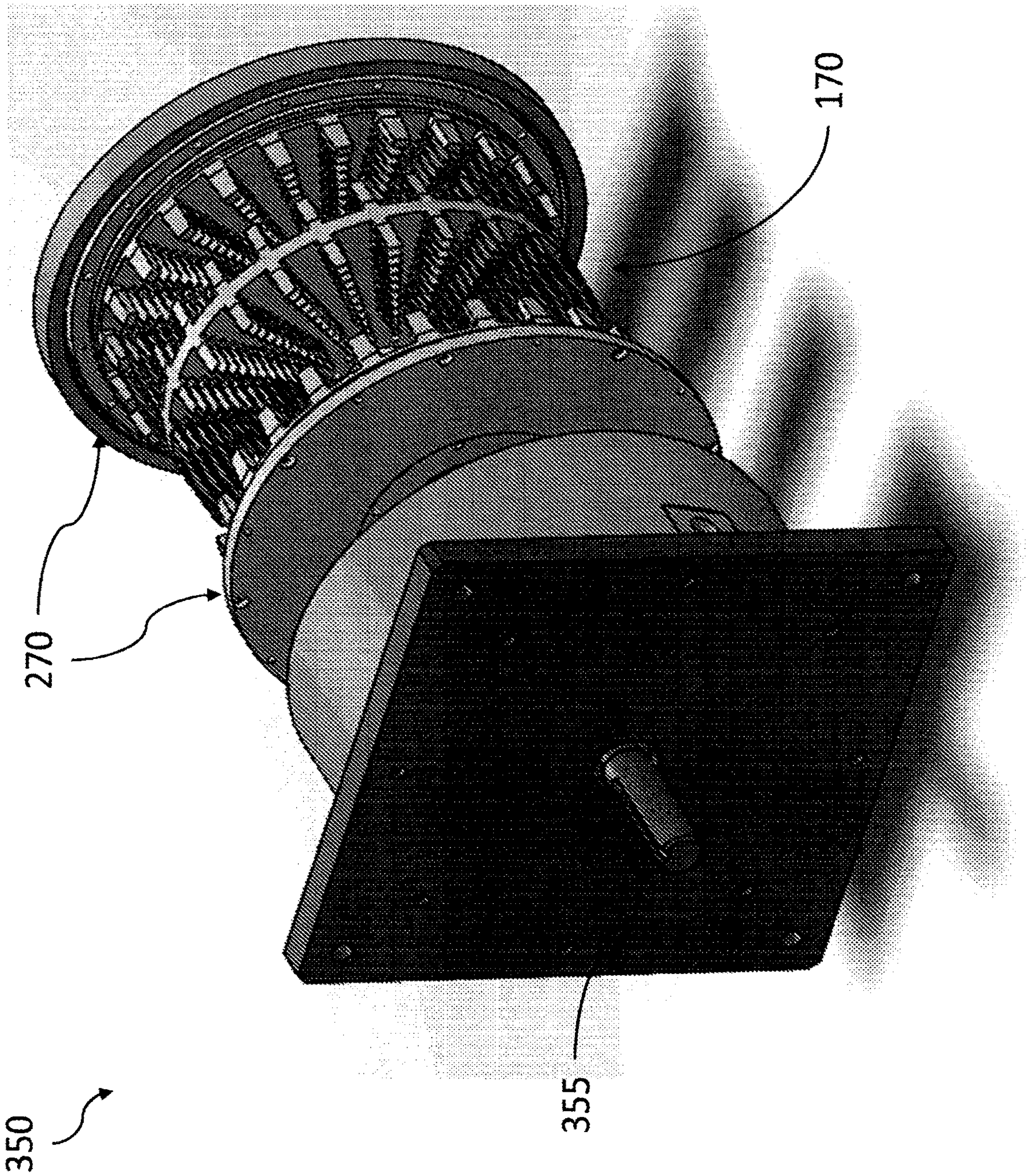
FIG. 3D is an illustration of an exploded view of a configuration of stators and rotors in accordance with an illustrative embodiment.

FIG. 3D is an illustration of an exploded view of a configuration of stators and rotors in accordance with an illustrative embodiment. The motor 350 includes two stator plates 270 and one rotor plate 170. In alternative embodiments, any suitable number of stator plates 270 and rotor plates 170 can be used. The stator plates 270 are fixed to a housing and do not rotate with respect to the housing. The rotor plate 170 is fixed to the shaft 355, both of which rotate with respect to the housing. The pegs 175 move past the pegs 275 as the rotor plate 170 rotates along the axis defined by the shaft 350.

In some embodiments, voltages of the stator plates 200 and rotor plates 100 can operate at different voltages. Some such embodiments can include variable capacitance machines. For example, a first portion (e.g., one third) of the stator plates 200 and a first portion (e.g., one third) of the rotor plates 100 can operate together at a first voltage, a second portion (e.g., one third) of the stator plates 200 and a second portion (e.g., one third) of the rotor plates 100 can operate together at a second voltage, and a third portion (e.g., one third) of the stator plates 200 and a third portion (e.g., one third) of the rotor plates 100 can operate together at a third voltage. In some embodiments, the nominal voltage of the first voltage, the second voltage, and the third voltage can be the same, but can differ in phase. For example, the first voltage, the second voltage, and the third voltage can each be out of phase with one another by 120°. The first portion of the rotor plates 100 can interleave with the first portion of the stator plates 200 along a first portion of a motor shaft, the second portion of the rotor plates 100 can interleave with the second portion of the stator plates 200 along a second portion of a motor shaft, and the third portion of the rotor plates 100 can interleave with the third portion of the stator plates 200 along a third portion of a motor shaft. The first portion of the rotor plates 100, the second portion of the rotor plates, and the third portion of the rotor plates 100 can each be rotationally skewed from one another. Similarly, the first portion of the stator plates 200, the second portion of the rotor plates 200, the third portion of the rotor plates 200 can each be rotationally skewed from one another. For example, each portion can be skewed by one third of the width of teeth 105 and/or teeth 205.

Figure 5A:
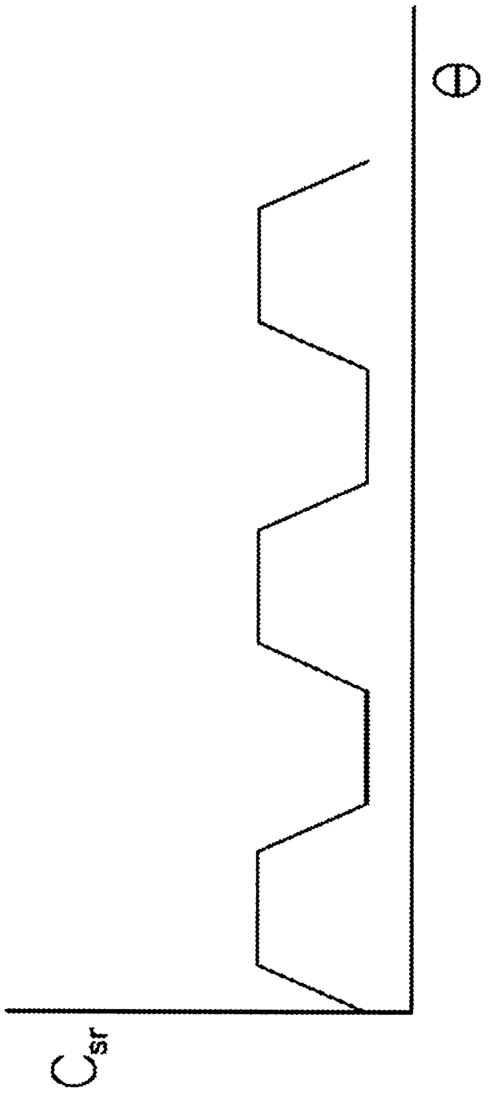
FIGS. 5A and 5B are plots of the capacitance between a stator and a rotor versus angular position in accordance with illustrative embodiments.
Figure 5B:
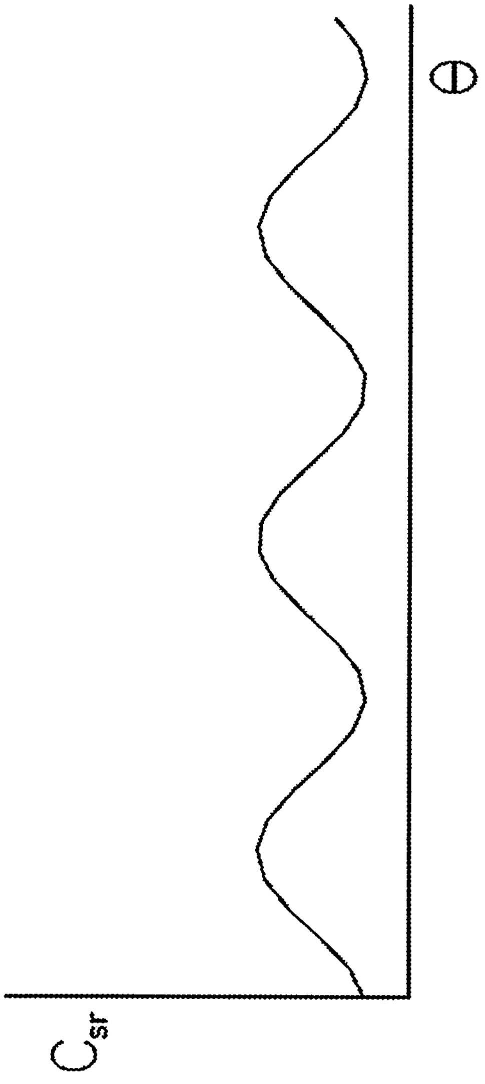

The shape of the teeth 105 and the teeth 205 can determine the profile capacitance waveform. FIGS. 5A and 5B are plots of the capacitance between a stator and a rotor versus angular position in accordance with illustrative embodiments. FIGS. 5A and 5B illustrate examples of profile capacitance waveforms. FIG. 5A illustrates a profile capacitance waveform for rotor plate 100 of FIG. 1A and stator plate 200 of FIG. 2A. FIG. 5B illustrates a profile capacitance waveform for rotor plate 100 of FIG. 1B and stator plate 200 of FIG. 2B.

The profile capacitance waveform can determine the corresponding torque waveform. The torque waveform form can be the derivative of capacitance with respect to the position of the rotor plate 100 and the stator plate 200. As the rotor plate 100 and stator plate 200 rotate in relation to one another, voltage can be applied to the rotor plate 100 and the stator plate 200 by a power electronic converter or other suitable device. In embodiments in which the capacitance varies as a trapezoidal waveform, such as in FIG. 5A, the applied voltage between the rotor plate 100 and the stator plate 200 by the power electronic converter can be a pulse or square waveform. In embodiments in which the capacitance varies as a sinusoidal waveform, such as in FIG. 5B, the applied voltage by the power electronic converter can be a sine wave.

Figure 4A:
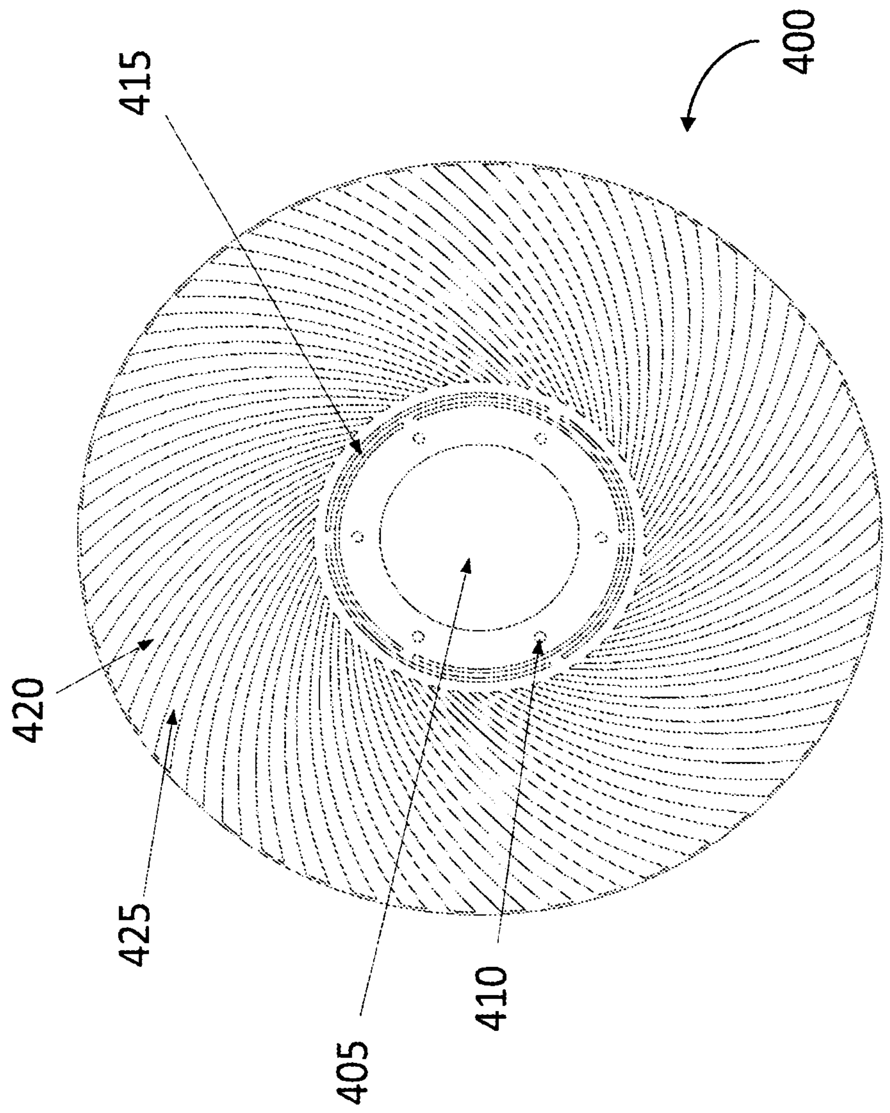
FIG. 4A illustrates a rotor with radial veins in accordance with an illustrative embodiment.
Figure 4B:
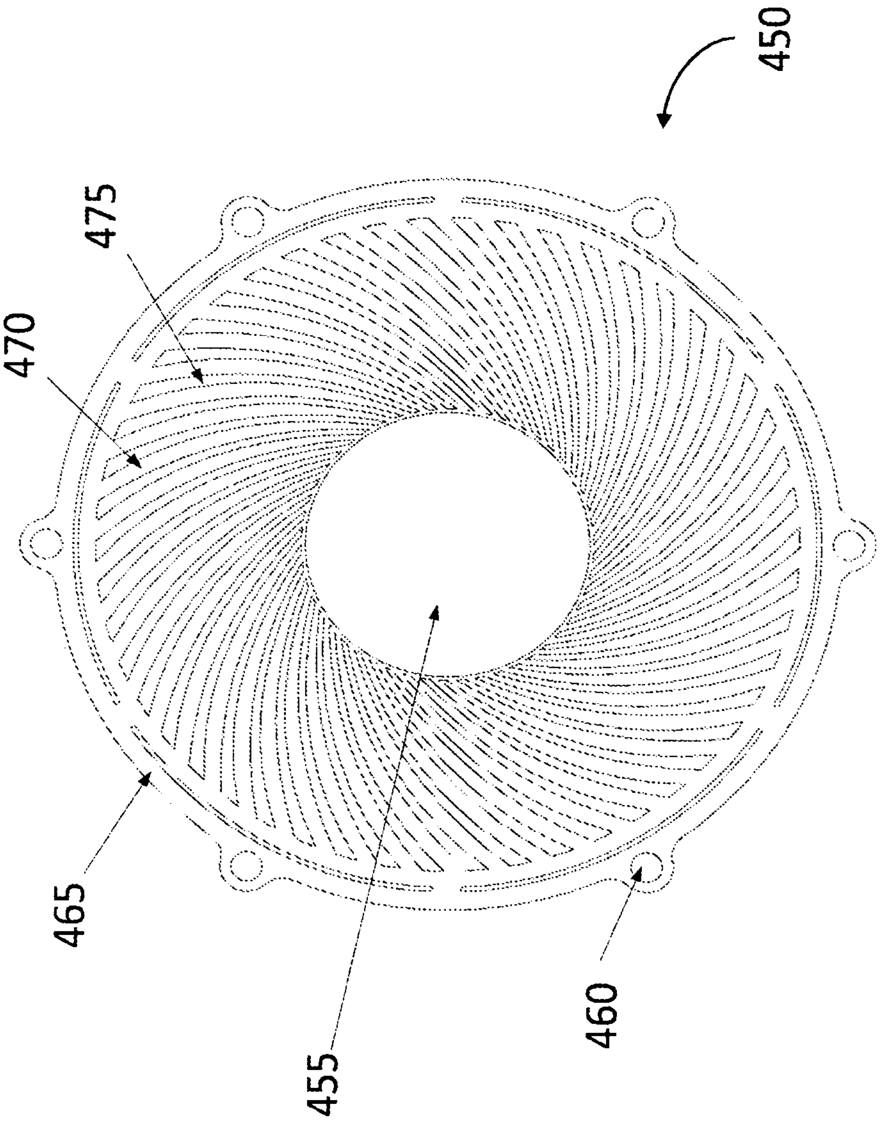
FIG. 4B illustrates a stator with radial veins in accordance with an illustrative embodiment.

The examples illustrated in FIGS. 5A and 5B represent switched and synchronous capacitance modes, respectively. As discussed above, such examples can be the result of using teeth 105 and teeth 205. In alternative embodiments, the stator and rotor plates may be stamped in such a way that spiral lines or veins intersect with one another. FIG. 4A illustrates a rotor with radial veins in accordance with an illustrative embodiment. FIG. 4B illustrates a stator with radial veins in accordance with an illustrative embodiment. In alternative embodiments, additional, fewer, and/or different elements can be used.

A rotor 400 can include a hollow center 405 through which a shaft can be inserted. Hub mounting holes 410 can be used to fix the rotor 400 to the shaft. Slits 415 can be formed in the rotor 400. The slits 415 can define flexure beams that allow the rotor 400 to flex axially. Spirals of the rotor 400 can include conducting sections 420 and insulating sections 425.

A stator 450 can include a hollow center 455 through which a shaft can be inserted. Plate mounting holes 460 can be used to rotationally fix the stator 450 such that the stator 450 is stationary with respect to a housing of the motor. Slits 465 can be formed in the rotor 450. The slits 465 can allow the stator 450 to flex axially. Spirals of the stator 450 can include conducting sections 470 and insulating sections 475.

Figure 4C:
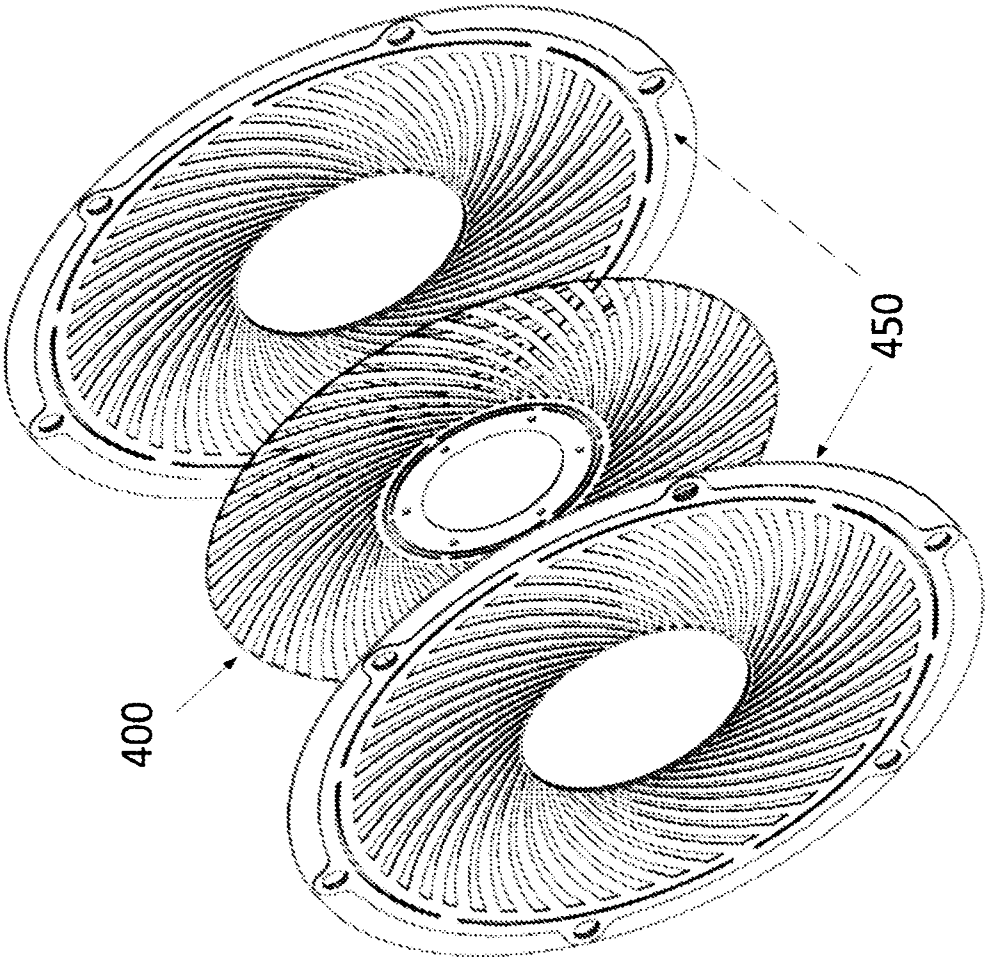
FIG. 4C is an illustration of an exploded view of a configuration of stators and rotors with radial veins in accordance with an illustrative embodiment.

FIG. 4C is an illustration of an exploded view of a configuration of stators and rotors with radial veins in accordance with an illustrative embodiment. In alternative embodiments, additional, fewer, and/or different elements can be used. As shown in FIG. 4C, a plurality of rotors 400 and stators 450 can be alternately stacked in a motor. In some embodiments, the direction of the spiral shape of each of the rotors 400 and stators 450 can be the same.

Figure 6:
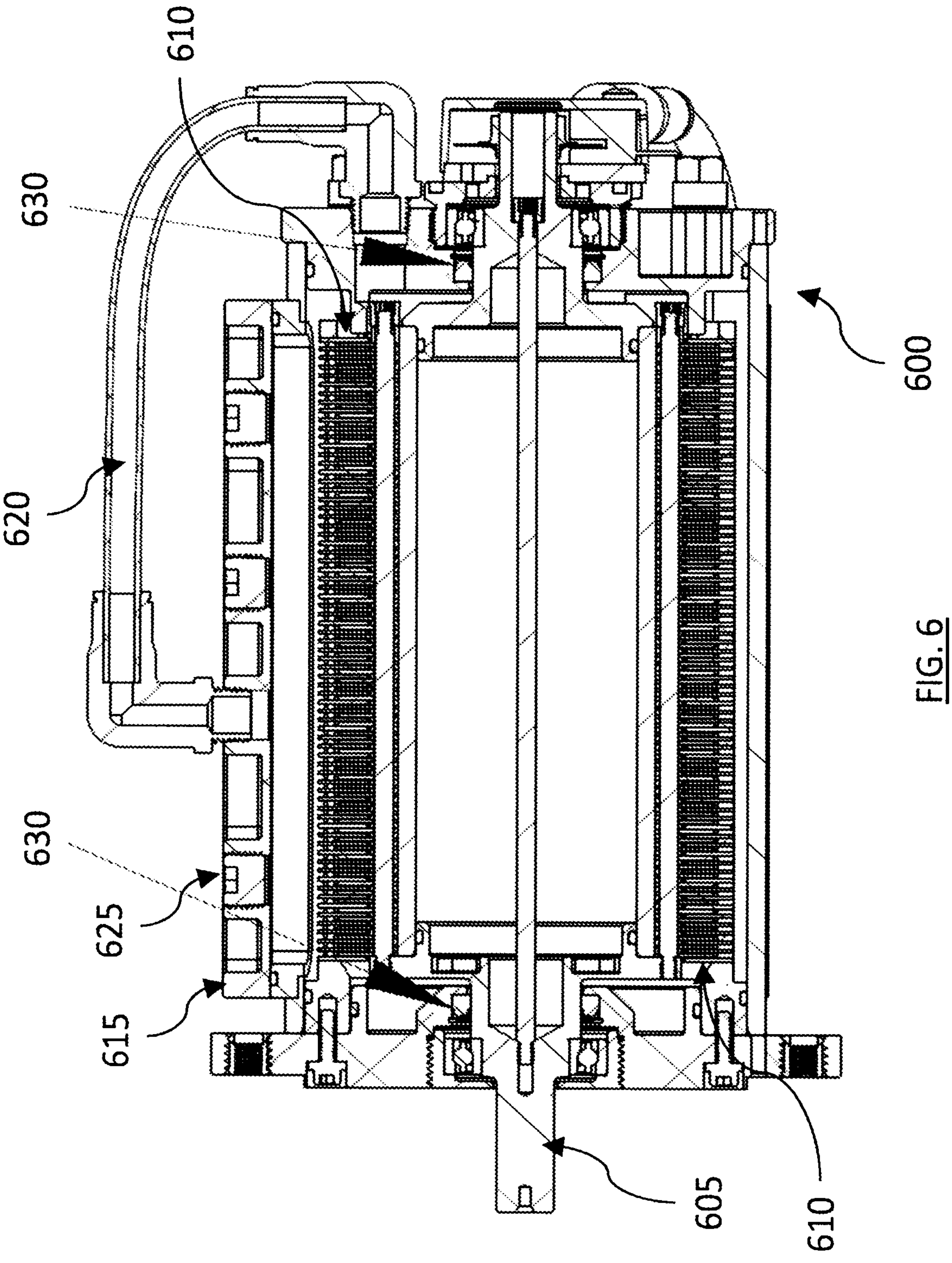
FIG. 6 is a cross-sectional view of an electrostatic machine in accordance with an illustrative embodiment.
Figure 7A:
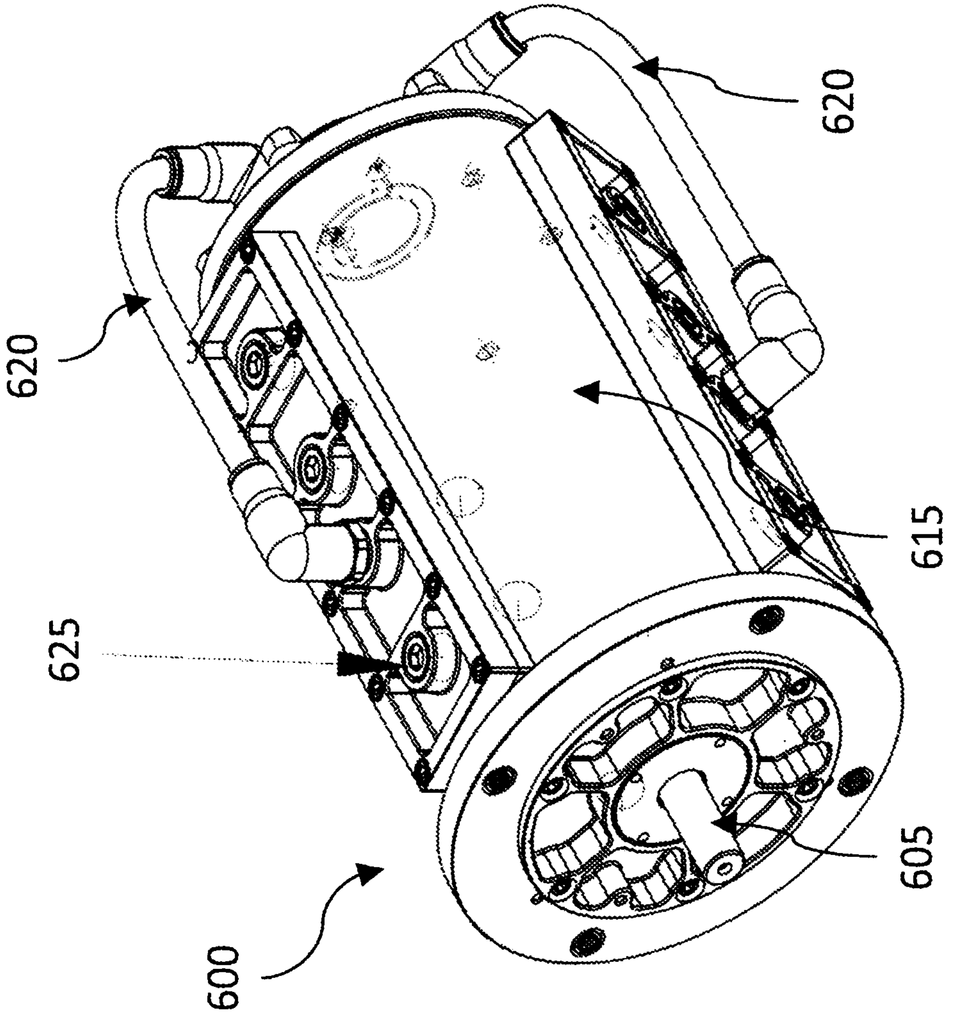
FIGS. 7A and 7B illustrate exterior views of an electrostatic machine in accordance with an illustrative embodiment.
Figure 7B:
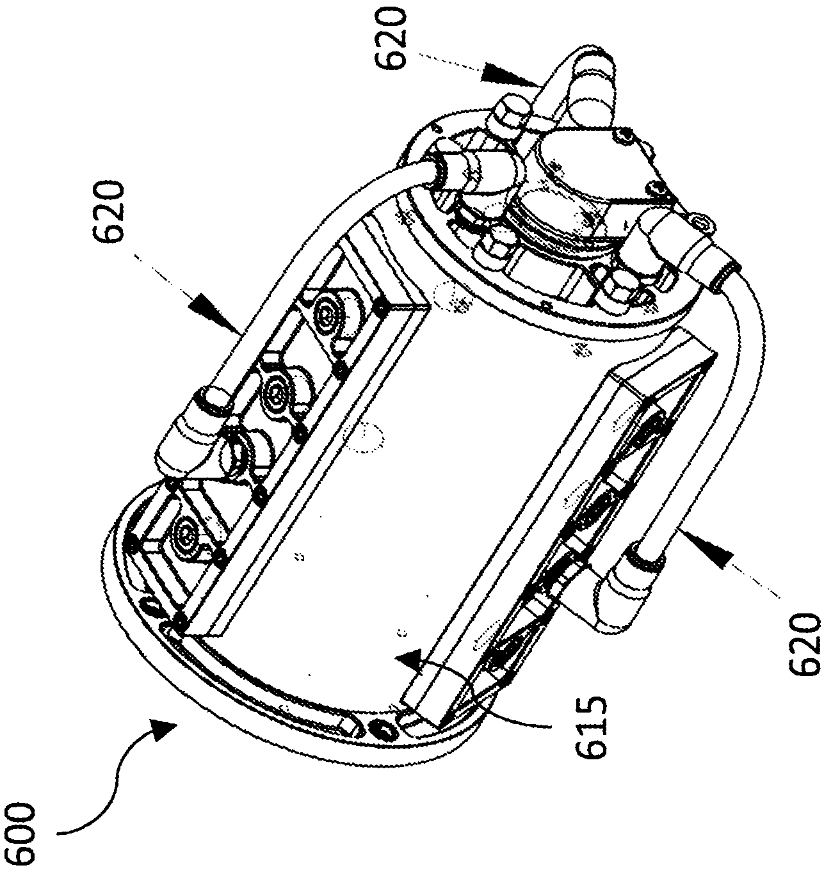
Figure 8:
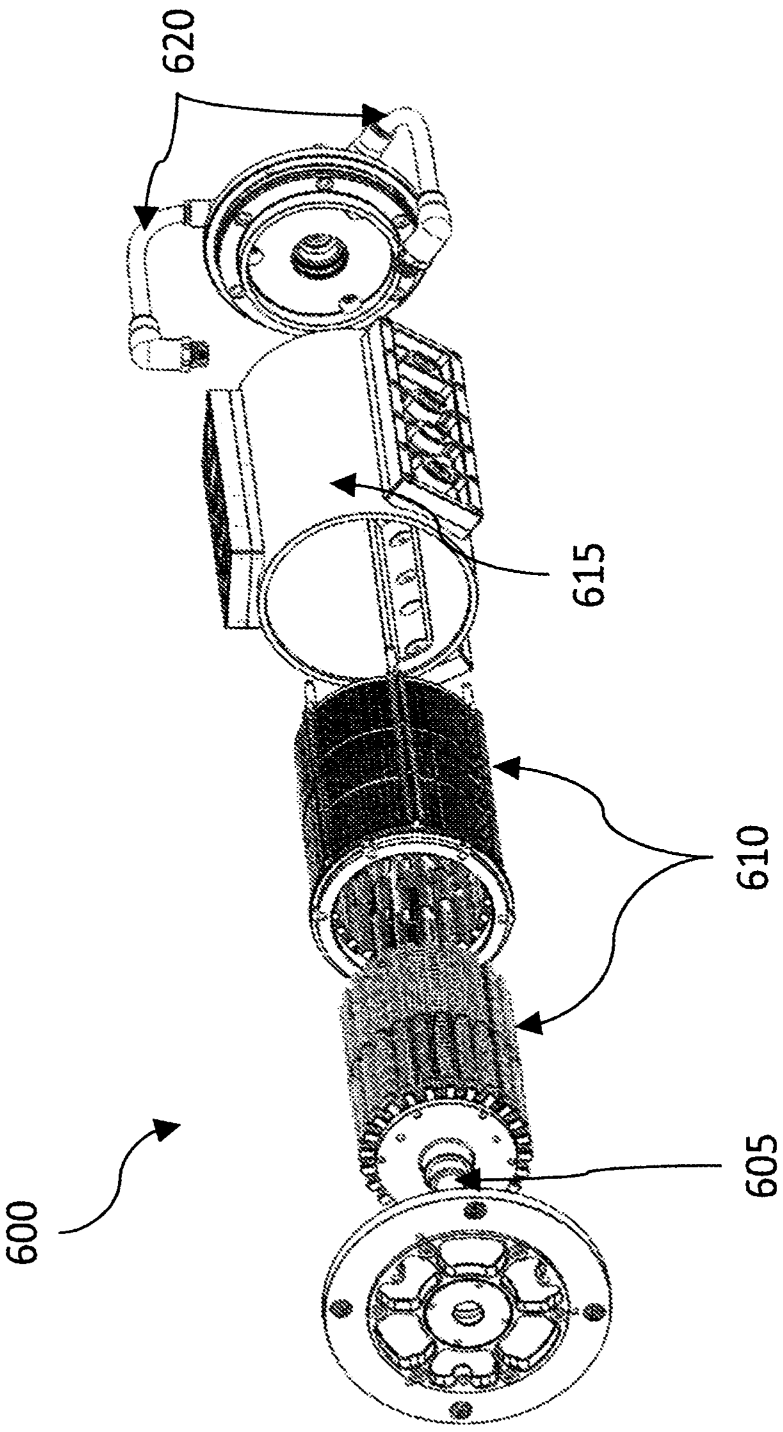
FIG. 8 is an illustration of an exploded view of some components of an electrostatic machine in accordance with an illustrative embodiment.

FIG. 6 is a cross-sectional view of an illustration of an electrostatic machine in accordance with an illustrative embodiment. FIGS. 7A and 7B illustrate exterior views of an electrostatic machine in accordance with an illustrative embodiment. FIG. 8 is an illustration of an exploded view of some components of an electrostatic machine in accordance with an illustrative embodiment. In alternative embodiment, additional, fewer, and/or different elements can be used. FIG. 6 is a cut-away view of a motor 600, FIGS. 7A and 7B are outside views of the motor 600, and FIG. 8 is an exploded view of the motor 600. The motor 600 can include a shaft 605, stator and rotor plates 610, a housing 615, a dielectric fluid recirculation path 620, fluid recirculation path connections 625, and seals 630.

Stators of the stator and rotor plates 610 can be rotationally fixed to the housing 615. Rotors of the stator and rotor plates 610 can be rotationally fixed to the shaft 605. The shaft 605 can rotate within the housing 615. The housing 615 can be filled with a dielectric fluid. The dielectric fluid can be recirculated through one or more recirculation paths 620. When the shaft 605 and, therefore, the rotor plates of the stator and rotor plates 610 are rotating, the dielectric fluid can be forced radially out and through the recirculation paths 620. The use of recirculation paths 620 can reduce the fluidic drag on the rotor plates of the stator and rotor plates 610. In some embodiments, the recirculation paths 620 can include a filter, a radiator, a heat exchanger, and/or other elements that can maintain and/or enhance performance of the dielectric fluid. The seals 630 can be configured to maintain fluid integrity of the housing 615 such that the shaft 605 can rotate while the housing 615 remains stationary, and the dielectric fluid can remain within the housing 615.

In some embodiments, rotor plates and/or stator plates can be stamped from a sheet of metal. For example, shapes illustrated in FIGS. 1A, 1B, 2A, 2B, 4A, and 4B can be stamped. Stamping the rotor plates and/or stator plates can assist in manufacturing and can allow mass production of the rotor plates and/or stator plates. In an alternative embodiment, the rotor plates and/or stator plates can be made of plastic with or without electrical conducting properties. For example, the rotor plates and/or stator plates may be created via injection molding or by three-dimensional printing. In an illustrative embodiment, a layer of metal is deposited onto the plastic plate surfaces to enhance electrical conducting properties of the plate.

Although FIGS. 1-7 illustrate electrostatic machines that use plates as electrodes, any suitable configuration of electrodes can be used. For example, electrostatic machines can be the same as or similar to those described in U.S. Pat. Nos. 3,094,653, 3,433,981, 6,353,276, and 8,779,647, which are incorporated herein by reference in their entirety. However, such examples are not meant to be limiting with respect to the type or configuration of electrostatic machines that can be used with the various dielectric fluids described herein. In alternative embodiments, electrostatic motors or actuators may be used. For example, any suitable electrostatic machine with a drive electrode (e.g., a rotor) and a stator electrode can be used. The drive electrode can move with respect to the stator electrode in any suitable fashion, such as via rotation (e.g., in the motor examples explained above) or linearly (e.g., in a linear actuator). The electrostatic machine can be used with any suitable combination of gears, clutches, engagement mechanisms, etc.

As noted above, a motor, such as motor 600, can convert electrical energy into rotational kinetic energy. The electrical energy can be three-phase alternating current (AC) power or pulsed direct current (DC) power. In some embodiments, direct current (DC) power can be converted into three-phase AC power, which can be used to power an electrostatic machine, such as electrostatic induction machines, variable capacitance/elastance machines, synchronous electrostatic machines, direct current (DC) electrostatic machines, and electrostatic hysteresis synchronous machines. The DC power can be converted into three-phase AC power by an inverter. A current sourced inverter (CSI) or a switched capacitor converter (SCC) can maintain a constant current output to a load, such as an electrostatic machine. A voltage sourced inverter (VSI) can maintain a constant voltage output to the load. In some embodiments, a CSI, an SCC, and/or a VSI may be pulse width modulated for a time-averaged variable output. In some embodiments, a CSI, an SCC, and/or a VSI may apply AC, DC, or pulsed DC voltages or currents to the load.

Some embodiments can use a VSI, an SCC, and/or a CSI to provide power to an electrostatic machine. In some embodiments, a CSI and/or an SCC can have significant advantages over a VSI when used with an electrostatic machine. In some instances, a VSI may not be directly connected to a variable capacitance machine because, in order to work most efficiently, a VSI can require inductive properties at the load terminals of the VSI, which the capacitance machine does not inherently have. However, a CSI and an SCC can have capacitive properties at the load terminals of the CSI/SCC in order to work most efficiently, which the capacitance machine does inherently have. Accordingly, in some embodiments, a CSI and/or an SCC can be directly connected to an electrostatic machine without the use of passive components (e.g., resistors, capacitors, inductors, etc.) between the inverter and the electrostatic machine.

Figure 9A:
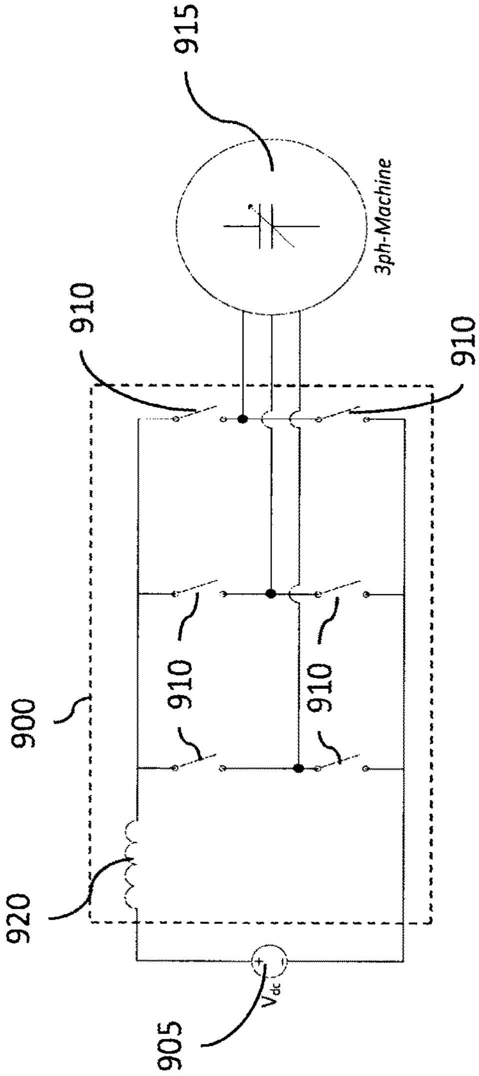
FIGS. 9A and 9B are circuit diagrams of a three-phase inverter and a three-phase machine in accordance with illustrative embodiments.
Figure 9B:
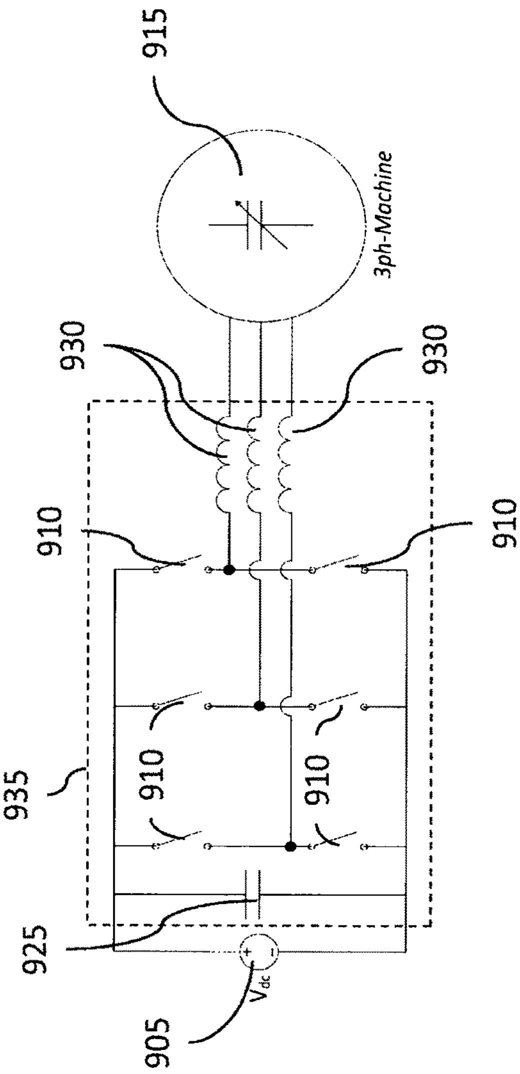
Figure 9C:
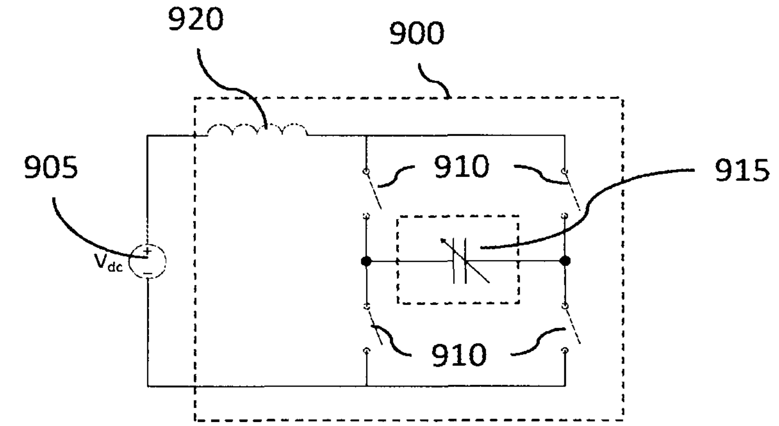
FIGS. 9C and 9D are circuit diagrams of a single-phase of a three-phase inverter in accordance with illustrative embodiments.
Figure 9D:
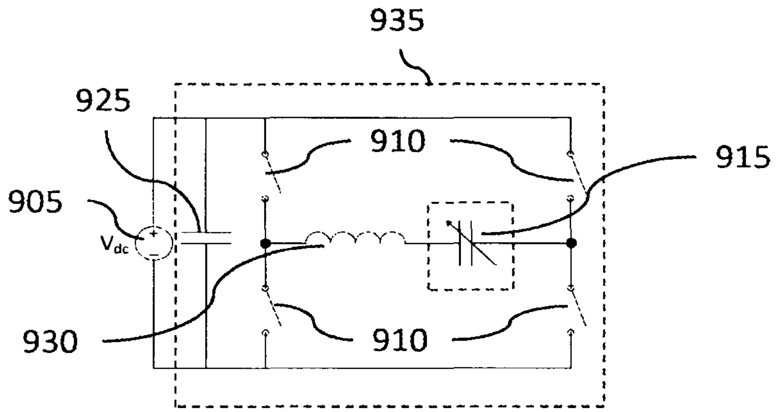

FIGS. 9A and 9B are circuit diagrams of a three-phase inverter and a three-phase machine in accordance with illustrative embodiments. FIGS. 9C and 9D are circuit diagrams of a single-phase of a three-phase inverter in accordance with illustrative embodiments. In alternative embodiments, additional, fewer, and/or different elements can be used. For example, although FIGS. 9A and 9B illustrate three-phase systems, any suitable multi-phase system can be used, such as two-phase, four-phase, five-phase, ten-phase, etc. FIG. 9A is a circuit diagram of a three-phase CSI used with a three-phase AC machine, such as an electrostatic machine, in accordance with an illustrative embodiment. FIG. 9C is a circuit diagram of a single phase of the three-phase CSI of FIG. 9A. Inverter 900 can be powered by a direct current power source 905 and can include a DC link inductor 920 and a plurality of switches 910. As illustrated in FIG. 9A, inverter 900 can be used to provide AC power to a three-phase AC machine 915, which can be an electrostatic machine. As illustrated in FIG. 9C, inverter 900 can be used to provide one phase of multi-phase AC power to the AC machine 915. The switches 910 can be controlled, for example by a controller, in any suitable manner such that the power of three electrical lines connected to the three-phase AC machine 915 is three-phase AC. In some embodiments, no passive components (e.g., resistors, capacitors, inductors, etc.) are used between the inverter 900 and the three-phase AC machine 915.

FIG. 9B is a circuit diagram of a three-phase voltage sourced inverter used with a three-phase AC machine, such as an electrostatic machine, in accordance with an illustrative embodiment. FIG. 9D is a circuit diagram of a single phase of the three-phase voltage sourced inverter of FIG. 9B. Inverter 935 can be powered by a direct current power source 905 and can include a DC link capacitor 925, a plurality of switches 910, and a plurality of inductors 930. As illustrated in FIG. 9B, inverter 935 can be used to provide AC power to a three-phase AC machine 915. As illustrated in FIG. 9D, inverter 935 can be used to provide one phase of multi-phase AC power to the AC machine 915. The switches 910 can be controlled, for example by a controller, in any suitable manner such that the power of three electrical lines connected to the three-phase AC machine 915 is three-phase AC.

Figure 9E:
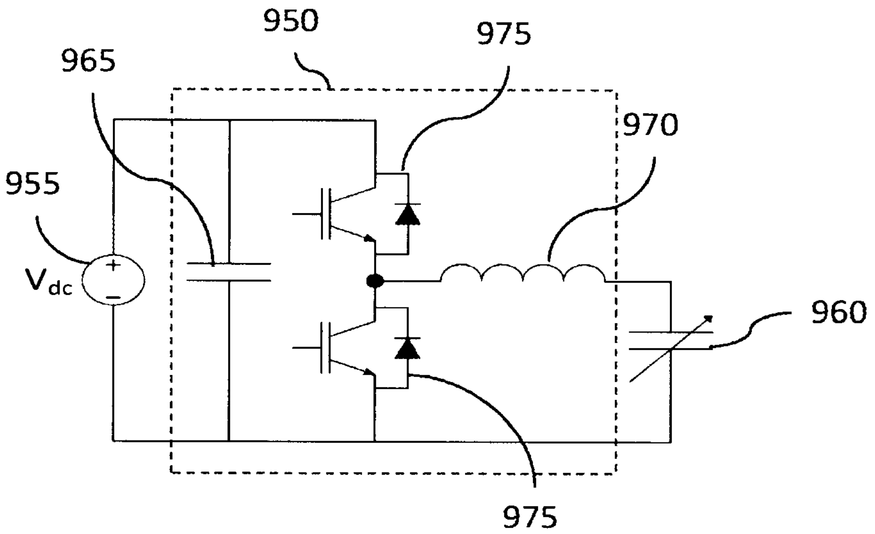
FIGS. 9E and 9F are circuit diagrams of a single-phase buck or boost converter of a three-phase inverter powering a single-phase of a three-phase machine in accordance with illustrative embodiments.
Figure 9F:
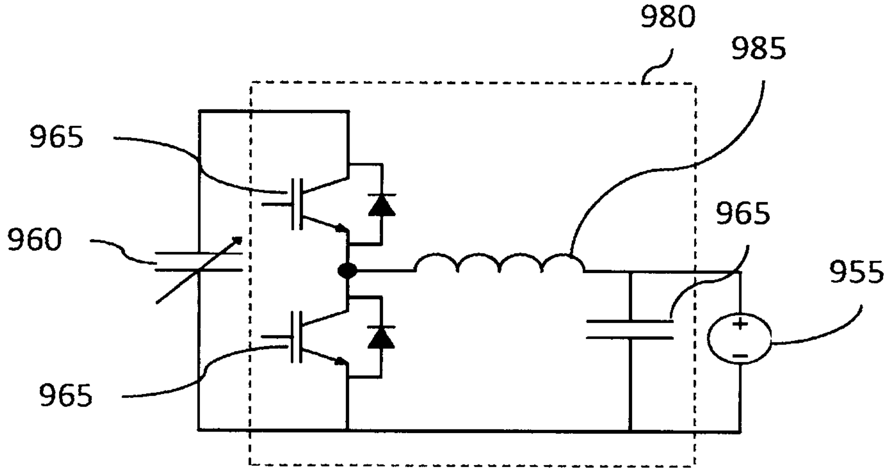

FIGS. 9E and 9F are circuit diagrams of a single-phase buck or boost converter of a three-phase inverter powering a single-phase of a three-phase machine in accordance with illustrative embodiments. In alternative embodiments, additional, fewer, and/or different elements can be used. FIGS. 9E and 9F are circuit diagrams of a single-phase voltage sourced buck or boost converter driving a single phase of a three-phase electrostatic machine, such as a variable capacitance electrostatic machine.

FIG. 9E illustrates an electrical power converter 950 that converts DC power from DC power source 955 into AC power or pulsed DC power for electrostatic machine 960. The converter 950 can include a DC link capacitor 965, switches 975, and an inductor 970. In the embodiment shown in FIG. 9E, switches 975 can include an insulated-gate bipolar transistor (IGBT) and a diode. In alternative embodiments, a metal-oxide-semiconductor field-effect transistors (MOSFET) and a diode can be used. In yet other embodiments, any suitable switching elements can be used, such as bipolar junction transistors (BJTs), thyristors, integrated gate commuted thyristors (IGCTs), reed switches, contactors, relays, etc. In some embodiments, switching elements can be used with a diode (e.g., as illustrated in FIG. 9E). In other embodiments, switching elements may not be used with a diode. As shown in FIG. 9E, the converter 950 is a half bridge, which can use fewer active semiconductor components than a full bridge. The configuration of the converter 950 illustrated in FIG. 9E can step-down (e.g., "buck") voltage from the DC power source 955 to the electrostatic machine 960. The configuration can recover energy back to the DC power source 955 by stepping-up (e.g., "boosting") voltage from the electrostatic machine 960. The stepping-up and stepping-down can be altered over time. In alternative embodiments, any switch described herein can be any suitable electronic or mechanical switch.

FIG. 9F illustrates a voltage sourced converter 980 that converts DC power from DC power source 955 into AC power for electrostatic machine 960. The converter 980 can include a DC link capacitor 965, switches 975, and an inductor 985. In the embodiment shown in FIG. 9F, switches 975 can include an IGBT and a diode. In alternative embodiments, a MOSFET and a diode can be used. As shown in FIG. 9F, the converter 980 is a half bridge, which can use fewer active semiconductor components than a full bridge. The configuration of the converter 980 illustrated in FIG. 9F can step-up (e.g., "boost") voltage from the DC power source 955 to the electrostatic machine 960. The configuration can recover energy back to the DC power source 955 by stepping-down (e.g., "bucking") voltage from the electrostatic machine 960. The stepping-up and stepping-down can be altered over time.

Figure 10A:
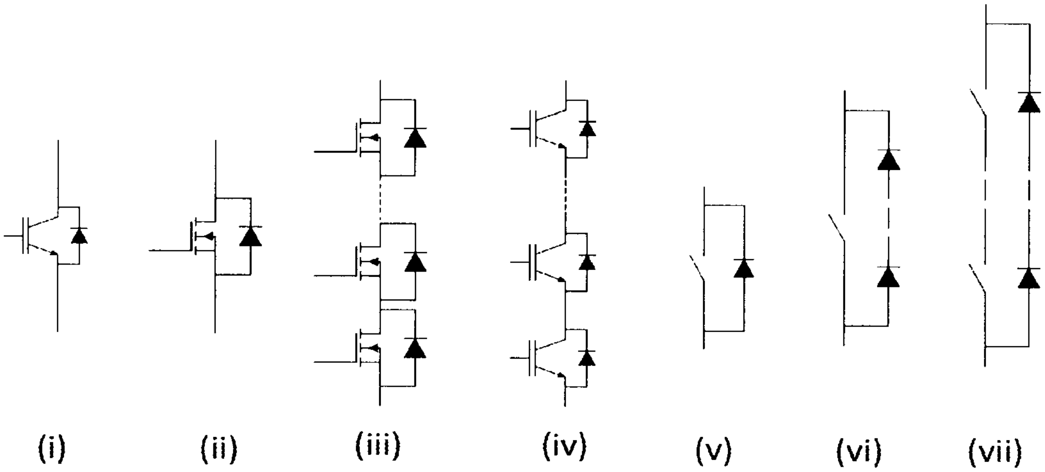
FIGS. 10A and 10B are diagrams of some examples of creating switches in accordance with illustrative embodiments.
Figure 10B:
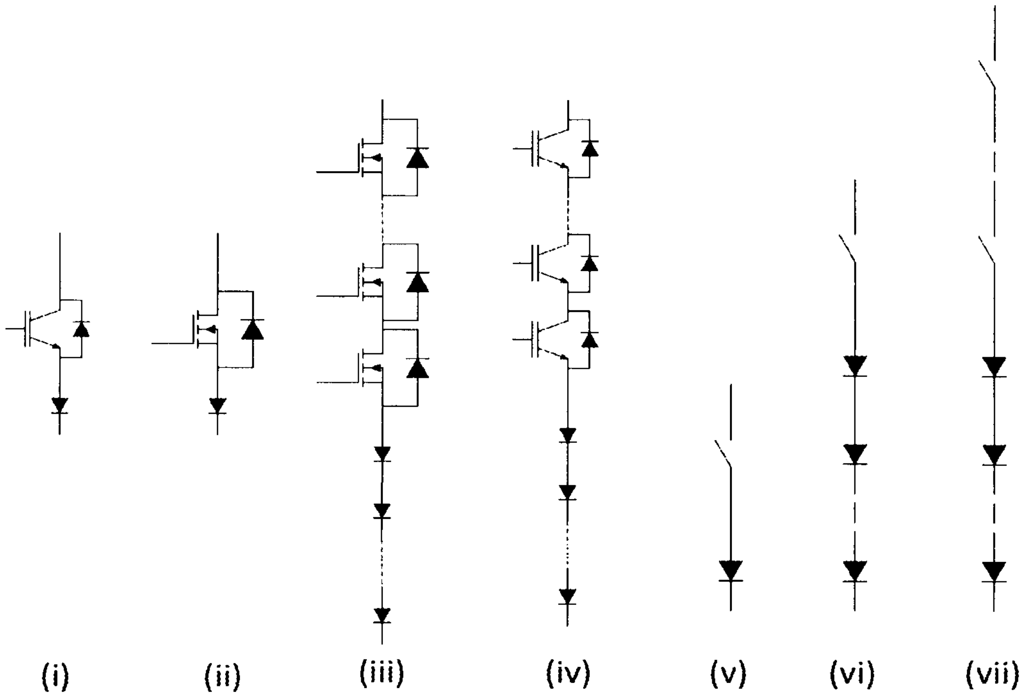

FIGS. 10A and 10B are diagrams of some examples of creating switches in accordance with illustrative embodiments. FIG. 10A provides some examples of producing switches of a voltage sourced inverter. FIG. 10B provides some examples of producing switches of a current sourced inverter. In some embodiments, the switches 910 can each be comprised of one or more semiconductor switches. The semiconductor switches can be able to block voltages greater than 500 Volts (V). In some embodiments, the semiconductor switches can comprise silicon (e.g., crystalline silicon) as the substrate of the switch. In alternative embodiments, the semiconductor switches can comprise wide bandgap semiconductors as the substrate of the switch, such as silicon carbide (SiC), Gallium Nitride (GaN), diamond, etc. In an illustrative embodiment, each switch 910 illustrated in FIGS. 9A-9F can be a silicon carbide semiconductor switch and a diode.

In an illustrative embodiment, each switch 910 illustrated in FIGS. 9B and 9D can be a single silicon carbide semiconductor switch and a diode, as illustrated in diagrams (i) and (ii) of FIG. 10A. In alternative embodiments, silicon semiconductor switches and/or diodes may be used. As illustrated in diagrams (i) and (iv) of FIG. 10A, in some embodiments, each switch 910 can comprise one or more IGBTs with a corresponding diode. As illustrated in diagrams (ii) and (iii) of FIG. 10A, in some embodiments, each switch 910 can comprise one or more MOSFETs with corresponding diodes. The diagrams of FIG. 10A can each block voltage in one direction and allow current to flow in either direction. Accordingly, the diagrams of FIG. 10A can be used as switches 910 in voltage sourced inverters. As illustrated in diagrams (iii) and (iv) of FIG. 10A, multiple switches illustrated in diagrams (ii) and (i), respectively, can be stacked in series to increase the voltage blocking capabilities of the switch 910.

As illustrated in diagrams (v) through (vii) of FIG. 10A, the switches 910 can include one or more physical switches and diodes in parallel. For example, diagram (v) shows an embodiment in which each switch includes one mechanical switch and one diode in parallel. Diagram (vi) shows an embodiment in which each switch 910 includes a mechanical switch in parallel with multiple (i.e., two or more) diodes that are each in series. In alternative embodiments, the diodes may be in parallel with one another. Diagram (vii) shows an embodiment in which each switch 910 includes multiple mechanical switches in parallel with multiple diodes. Depending upon the embodiment, the number of mechanical switches may or may not equal the number of diodes for each switch 910. In alternative embodiments, any suitable configuration can be used.

In some embodiments, additional passive and/or active components may be added to each switch such that the voltage across each switch is about the same. For example, resistors can be connected in parallel with each switch. In alternative embodiments, any suitable combination or use of diodes, resistors, capacitors, etc. can be used to equalize voltage across each switch.

In an illustrative embodiment, each switch 910 illustrated in FIGS. 9A and 9C can be a single silicon carbide semiconductor switch and a diode, as illustrated in diagrams (i) and (ii) of FIG. 10B. In alternative embodiments, silicon semiconductor switches and/or diodes may be used. As illustrated in diagrams (i) and (iv) of FIG. 10B, in some embodiments, each switch 910 can comprise one or more IGBTs with a corresponding diode and one or more diodes in series with the IGBTs and their corresponding diodes. As illustrated in diagrams (ii) and (iii) of FIG. 10B, in some embodiments, each switch 910 can comprise one or more MOSFETs with corresponding diodes and one or more diodes in series with the MOSFETs and their corresponding diodes. The diagrams of FIG. 10B can each conduct current in one direction and block voltage in both directions. Accordingly, the diagrams of FIG. 10A can be used as switches 910 in current sourced inverters. As illustrated in diagrams (iii) and (iv) of FIG. 10B, multiple switches illustrated in diagrams (ii) and (i), respectively, can be stacked in series to increase the voltage blocking capabilities of the switch 910.

As illustrated in diagrams (v) through (vii) of FIG. 10B, the switches 910 can include one or more physical switches and diodes in series. For example, diagram (v) shows an embodiment in which each switch includes one mechanical switch and one diode in series with one another. Diagram (vi) shows an embodiment in which each switch 910 includes a mechanical switch in series with multiple (e.g., two or more) diodes that are each in series. In alternative embodiments, the diodes may be in parallel with one another. Diagram (vii) shows an embodiment in which each switch 910 includes multiple mechanical switches in parallel with each other and with multiple diodes. Depending upon the embodiment, the number of mechanical switches may or may not equal the number of diodes for each switch 910. In alternative embodiments, any suitable configuration can be used. In some embodiments, additional passive and/or active components may be added to each switch such that the voltage across each switch is about the same.

Figure 11A:
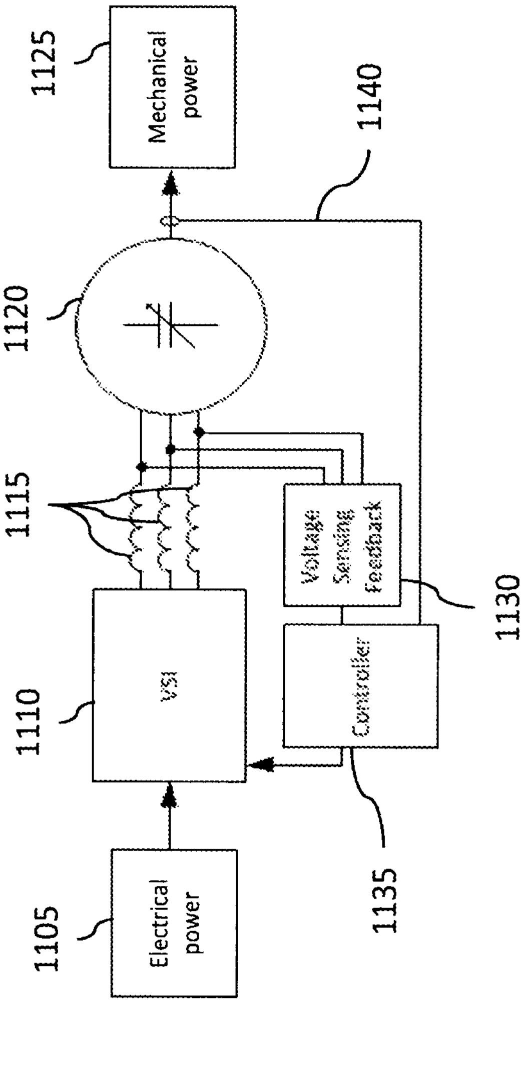
FIGS. 11A and 11B are block diagrams of a capacitive machine drive control system in accordance with illustrative embodiments.
Figure 11B:
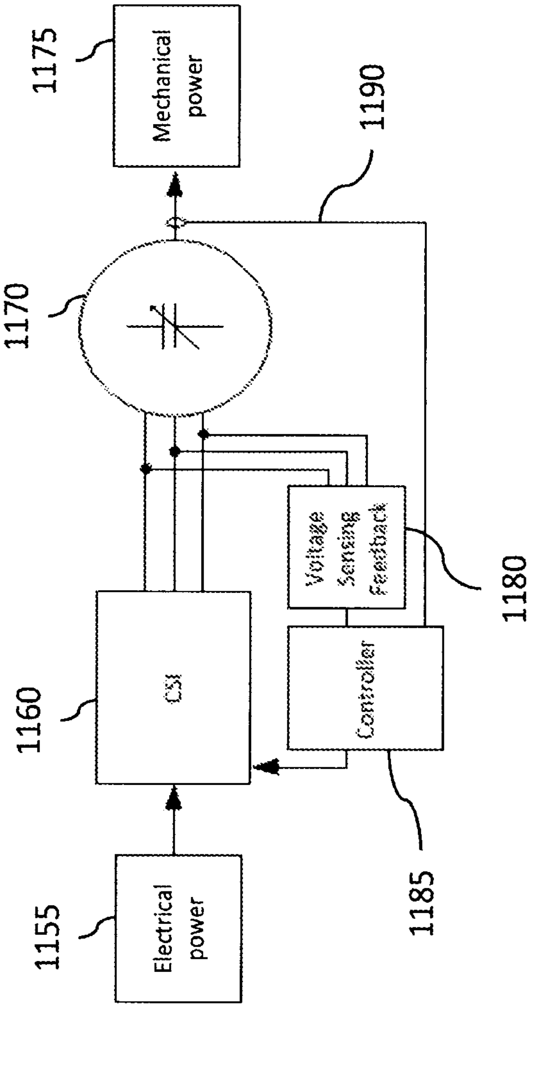

FIGS. 11A and 11B are block diagrams of a capacitive machine drive control system in accordance with illustrative embodiments. In alternative embodiments, additional, fewer, and/or different elements may be used. Also, the use of arrows between elements is not meant to be limiting with respect to the direction of energy flow. FIG. 11A is a block diagram of an embodiment of controlling a three-phase machine powered by a VSI power source. A system 1100 can include electrical power 1105, a VSI 1110, inductors 1115, a machine 1120, mechanical power 1125, a voltage sensing feedback 1130, a controller 1135, and a position sensing line 1140. As illustrated in FIG. 11A, electrical power 1105 can be input into system 1100 and mechanical power 1125 can be output from the system 1100. In alternative embodiments, mechanical power 1125 can be input into system 1100 and electrical power 1105 can be output from the system 1100 (e.g., by using machine 1120 as a generator). Further, although FIG. 11A illustrates a three-phase system, any suitable number of phases can be used. The machine 1120 can be a multi-phase electrostatic machine.

Electrical power 1105 can be input into VSI 1110. In some embodiments, the electrical power 1105 can be direct current power and VSI 1110 can be a voltage-sourced inverter such as inverter 935. The power of the electrical connections between the VSI 1110 and the machine 1120 can have an alternating voltage. Inductors 1115 can be placed in each leg of the electrical connections between the VSI 1110 and the machine 1120.

The voltage sensing feedback 1130 can be used in a control loop. The voltage sensing feedback 1130 can use one or more sensors to sense a voltage across stator electrodes and rotor electrodes of the machine 1120. The voltage sensing feedback 1130 can send a signal to the controller 1135 indicating the sensed voltage. The controller 1135 can compare the sensed voltage to a setpoint voltage. Based on the comparison, the controller 1135 can indicate a change in the switching of VSI 1110. The controller 1135 can use a proportional control loop, an integral control loop, a derivative control loop, or any combination thereof.

The amount of torque output by the machine 1120 can be dependent upon the voltage signal applied across the stator electrodes and the rotor electrodes of the machine 1120. Accordingly, the controller 1135 can modify the torque output by the machine 1120 by indicating a change in the switching of the VSI 1110. In some embodiments, the voltage signal sensed by the voltage sensing feedback 1130 can be an alternating voltage signal. Similarly, the setpoint voltage can be an alternating voltage signal. The indication of a change in switching of the VSI 1110 output by the voltage sensing feedback 1130 can include an indication of a change in frequency, amplitude, phase, etc.

As shown in FIG. 11A, a position sensing line 1140 can be used to input a position of the shaft of the machine 1120 into the controller 1135. The controller 1135 can use the rotational direction of the shaft of the machine 1120 to determine what voltage should be applied to the machine 1120. For example, the position sensing line 1140 can be used to alter amplitude, phase, frequency, etc. of the voltage across the stator electrodes and the rotor electrodes. In some embodiments, the controller 1135 can be controller 1200, discussed in greater detail below.

FIG. 11B is a block diagram of an embodiment of controlling a three-phase machine powered by a CSI power source. A system 1150 can include electrical power 1155, a CSI 1160, a machine 1170, mechanical power 1175, a voltage sensing feedback 1180, a controller 1185, and a position sensing line 1190. As illustrated in FIG. 11B, electrical power 1155 can be input into system 1150 and mechanical power 1175 can be output from the system 1150. In alternative embodiments, mechanical power 1175 can be input into system 1150 and electrical power 1155 can be output from the system 1150 (e.g., by using machine 1150 as a generator). Further, although FIG. 11B illustrates a three-phase system, any suitable number of phases can be used. The machine 1120 can be a multi-phase electrostatic machine.

Electrical power 1155 can be input into CSI 1110. In some embodiments, the electrical power 1155 can be direct current power and CSI 1110 can be a current-sourced inverter such as inverter 900. The power of the electrical connections between the CSI 1110 and the machine 1170 can have an alternating voltage. The voltage sensing feedback 1180 can be used in a control loop with controller 1185 and position sensing line 1190, which can operate as explained above with respect to FIG. 11A.

Figure 11C:
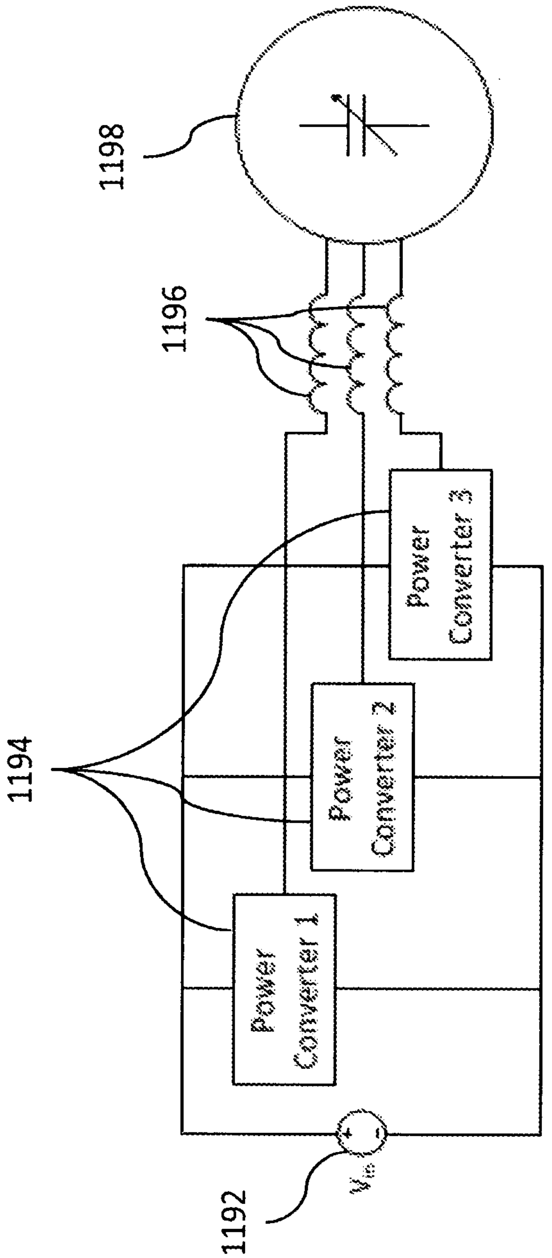
FIG. 11C is a block diagram of a circuit architecture for powering an electrostatic machine in accordance with an illustrative embodiment.

FIG. 11C is a block diagram of a circuit architecture for powering an electrostatic machine in accordance with an illustrative embodiment. In alternative embodiments, additional, fewer, and/or different elements can be used. A circuit can include a power source 1192, a plurality of power converters 1194, inductors 1196, and a machine 1198. As discussed above, power source 1192 can be a direct current power source. Power converters 1194 can be configured to convert power from power source 1192 into alternating voltage power for use by the machine 1198. In some embodiments, the power converters 1194 can be configured to convert power produced by the machine 1198 into electrical power, such as direct current electrical power. In the embodiment illustrated in FIG. 11C, a three-phase system is shown. However, any suitable number of phases can be used. The machine 1198 can be a multi-phase electrostatic machine.

The power converters 1194 can be any suitable power converter, including a VSI, SCC, or CSI power converter. As illustrated in FIG. 11A, the power converters 1194 can be in parallel with one another and can be configured to each provide a power phase to the machine 1198. Inductors 1196 are illustrated in each phase of the machine 1198. However, in alternative embodiments, inductors 1196 may not be used.

To scale electrostatic machines up to produce greater than 1 horsepower, medium to high voltage can be used. For example, voltages greater than 1000 V can be used between rotor plates and stator plates. Electrostatic induction machines, variable capacitance/elastance machines, synchronous electrostatic machines, and electrostatic hysteresis synchronous machines can use medium to high AC power. Direct current (DC) electrostatic machines and corona machines can use high voltage DC power. For electrostatic machines that can create greater than one quarter horsepower and less than one megawatt (MW) (e.g., about 1,341 horsepower), high voltage power electronic drives can be used. However, high voltage variable frequency AC or pulsed DC power sources, which can also be suitable for use with electrostatic machines, are not generally commercially available.

However, as described above with reference to FIGS. 9A-9F and 10A and 10B, various high voltage variable frequency AC or pulsed DC power sources can be used. The use of a high voltage variable frequency AC or pulsed DC power source can make electromagnetic machines with greater than one quarter horsepower output practical and useable in commercial and/or industrial applications.

Electrostatic machines can be used in a variety of applications. Electrostatic machines that can produce less than 1 horsepower can be efficient and compact. However, scaling up the size of electrostatic machines can produce hurdles in implementation.

In some instances, breakdown of the dielectric fluid can occur in the gap between the surfaces of the stator plate and the rotor plate. Torque is proportional to the square of the gap electric field. The gap electric field strength is proportional to the voltage applied across the stator plate and the rotor plate. Breakdown of the dielectric fluid can lead to arcing between the stator plate and the rotor plate. Arcing events can reduce the amount of torque that may be developed. Breakdown of the dielectric fluid can pose a problem in electrostatic induction machines, variable capacitance/elastance machines, synchronous electrostatic machines, direct current (DC) electrostatic machines, and electrostatic hysteresis synchronous machines. In some embodiments, an ultra-high vacuum (e.g., less than $10^{-2}$ Torr) can be used within the housing of the electrostatic machines to prevent arcing. However, the cost of vacuum pumps, bearing vacuum seals, etc. can be cost prohibitive. Further, the loss of the relative permittivity material in the gap between the stator plates and the rotor plates can reduce the effectiveness of the machine.

A gap displacement field of an electrostatic motor can be the displacement field in the gap between the stator plates and the rotor plates. The gap displacement field strength can be proportional to the relative permittivity of the medium filling the gap. Fluids with appreciable relative permittivity (e.g., greater than 7) and/or with low electrical conductivity (e.g., $10^{-9}$ Siemens per centimeter (S/cm)) that are chemically and electrically stable and/or suitable can be used to enhance the efficiency of the machine. Enhancing the gap displacement field can be beneficial to electrostatic induction machines, variable capacitance/elastance machines, synchronous electrostatic machines, direct current (DC) electrostatic machines, and electrostatic hysteresis synchronous machines by increasing the electrostatic shear force in the gap for a given voltage.

Accordingly, a fluid that can fill the gap between stator plates and rotor plates of an electrostatic machine that has a high permittivity, low conductivity, low viscosity, is chemically stable and suitable for machine components, and is electrically stable and suitable for machine components can be beneficial to electrostatic machines. In some embodiments, beneficial properties for a fill fluid can also include practical properties such as low toxicity and low flammability. The fill fluid may be a dielectric fluid.

In some embodiments, a high viscosity fluid may be used. For example, in embodiments in which the machine has a short rotation or stroke length (e.g., in a linear actuator) in which removal of rotational or linear power from the machine is to be quickened. Depending upon the embodiment, any suitable properties can be chosen.

Fluids with a high permittivity fluid can have a molecular structure that has a high dipole moment. In some instances, strong dipole-dipole interactions can generally lead to a higher viscosity and a higher boiling point. For example, increasing the number of carbons in the carbon chain typically increases the dipole moment and in turn increases the viscosity. However, increasing the branching of a carbon chain may not increase the dipole moment. Alternatively, a low permittivity fluid may be induced to have a higher dipole moment and in turn a higher viscosity. In some embodiments, a higher dipole moment may be induced through the introduction of a strong electric field. Therefore, some fluids with high permittivity may also have relatively high viscosity and some fluids with low permittivity may also have a relatively high viscosity.

In many instances, high permittivity fluids have inherently high conductivities. Some commercially available high permittivity liquids that are 99.5% pure contain too many contaminants to be useful as a dielectric fluid within electrostatic machines. The presence of trace amounts of ions, gas, and/or highly mobile molecules can lead to unacceptably high electrical losses and/or premature breakdown.

In some embodiments, liquids with a high permittivity can be purified using suitable techniques. For example, purification may be carried out by dehydration, degasification, distillation, or ion removal. In some embodiments, a high voltage insulator can have ionic conductivities that are less than $10^{12}$ S/cm.

In any of the above embodiments, an ester may be used as the dielectric fluid. Illustrative esters include those of formula RC(O)O—R', wherein R and R' are individually a substituted or unsubstituted alkyl or alkenyl group. In some embodiments, R may be a substituted or unsubstituted $C_1$-$C_{30}$ alkyl or alkenyl group. In some embodiments, R may include one or more carbon-carbon double bonds. In some embodiments, R may include two or more carbon-carbon double bonds. In some embodiments, the carbon-carbon double bonds may be trans. In some embodiments, R may include one or more alkyl branching groups. In some embodiments, the one or more branching groups may include a substituted or unsubstituted $C_1$-$C_6$ alkyl group. In some embodiments, the one or more alkyl branches may include a $C_1$-$C_3$ alkyl group. In some embodiments, R may be a substituted or unsubstituted $C_1$-$C_{24}$ alkyl or alkenyl group. In some embodiments, R may be a substituted or unsubstituted $C_1$-$C_{12}$ alkyl or alkenyl group. In some embodiments, R may be a substituted or unsubstituted $C_1$-$C_{10}$ alkyl group. In some embodiments, R may be a substituted or unsubstituted $C_2$-$C_{12}$ alkenyl group. In some embodiments, R may be a substituted or unsubstituted methyl, pentyl, hexyl, octyl, pentenyl, hexenyl, or octenyl group optionally substituted with one or more alkyl branching groups. In some embodiments, R may be an pentyl, hexyl, pentenyl, or octenyl group optionally substituted with one or more alkyl branching groups. In some embodiments, the octenyl group may include two or more carbon-carbon double bonds. In some embodiments, the octenyl group may include one or more $C_1$-$C_6$ alkyl branching groups. In some embodiments, the one or more alkyl branches may include a $C_1$-$C_3$ alkyl group. In some embodiments, the octenyl group may be a 3,7-dimethyl-2,6-octadienyl group ("geranyl group"). In some embodiments, R may be a pentyl, geranyl, or hexyl group.

In some embodiments, R' may be a substituted or unsubstituted $C_1$-$C_{30}$ alkyl or alkenyl group. In some embodiments, R' may include one or more carbon-carbon double bonds. In some embodiments, the carbon-carbon double bonds may be trans. In some embodiments, R' may be a substituted or unsubstituted $C_1$-$C_{24}$ alkyl or alkenyl group. In some embodiments, R' may be a substituted or unsubstituted $C_1$-$C_{12}$ alkyl or alkenyl group. In some embodiments, R' may include one or more alkyl branching groups. In some embodiments, the branching groups may include a substituted or unsubsituted $C_1$-$C_6$ alkyl group. In some embodiments, the branching groups may include a substituted or unsubsituted $C_1$-$C_3$ alkyl group. In some embodiments, R' may be a substituted or unsubstituted $C_1$-$C_{10}$ alkyl group or a substituted or unsubstituted $C_2$-$C_{10}$ alkenyl group. In some embodiments, R' may be a methyl, ethyl, propyl, isopropyl, or pentenyl group. The pentenyl group may include one or more $C_1$-$C_6$ alkyl branching groups. In some embodiments, the one or more alkyl branches may include a $C_1$-$C_3$ alkyl group. In some embodiments, the pentyl group may be a 4,4-dimethyl-pentyl group. In some embodiments, the pentenyl group may be a 4,4-dimethyl-2-pentenyl group.

In some embodiments, R and R' are individually a substituted or unsubstituted $C_1$-$C_{30}$ alkyl or alkenyl group. In some embodiments, R and R' are individually a substituted or unsubstituted $C_1$-$C_{24}$ alkyl or alkenyl group. In some embodiments, R and R' are individually a substituted or unsubstituted $C_1$-$C_{12}$ alkyl or alkenyl group. In some embodiments, R may be a substituted or unsubstituted $C_5$-$C_{30}$ alkyl group or a substituted or unsubstituted $C_5$-$C_{30}$ alkenyl group; and R' may be a substituted or unsubstituted $C_1$-$C_3$ alkyl group. In some embodiments, R may be a substituted or unsubstituted $C_5$-$C_{10}$ alkyl group or a substituted or unsubstituted $C_5$-$C_{12}$ alkenyl group; and R' may be a substituted or unsubstituted $C_1$-$C_3$ alkyl group. In some embodiments, R' may be a substituted or unsubstituted $C_5$-$C_{30}$ alkyl group or a substituted or unsubstituted $C_5$-$C_{30}$ alkenyl group; and R may be a substituted or unsubstituted $C_1$-$C_3$ alkyl group. In some embodiments, R' may be a substituted or unsubstituted $C_5$-$C_{10}$ alkyl group or a substituted or unsubstituted $C_5$-$C_{12}$ alkenyl group; and R may be a substituted or unsubstituted $C_1$-$C_3$ alkyl group. In some embodiments the ester may be selected from the group consisting of:

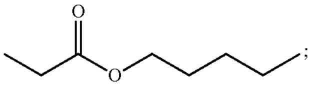;

pentyl propionoate

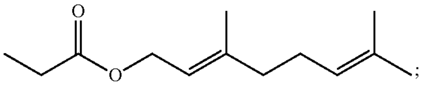;

geranyl propionoate

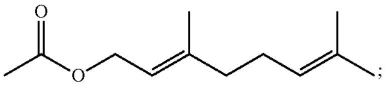;

geranyl acetate

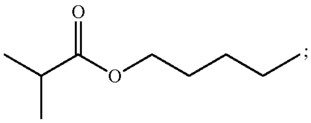;

pentyl isobutyrate

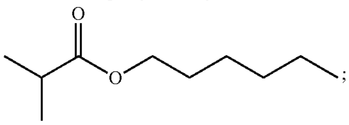;

hexyl isobutyrate

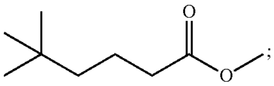;

methyl 5,5-dimethylhexanoate

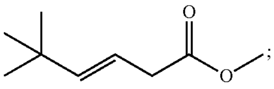;

methyl (*E*)-5,5-dimethylhex-3-enoate and combinations of two or more thereof.

Illustrative esters also include those of formula $R^C$—O(O)CH$R^B$(O)O—$R^A$, wherein $R^A$ and $R^C$ are individually a substituted or unsubstituted alkyl or alkenyl group and $R^B$ is a substituted or unsubstituted alkylene group. In some embodiments, $R^A$ and $R^C$ are individually a substituted or unsubstituted $C_1$-$C_{12}$ alkyl group. In some embodiments, $R^A$ and $R^C$ are individually a substituted or unsubstituted $C_1$-$C_6$ alkyl group. In some embodiments, $R^A$ and $R^C$ are individually a substituted or unsubstituted $C_1$-$C_3$ alkyl group. In some embodiments, $R^A$ and $R^C$ are methyl. In some embodiments, $R^B$ may be a substituted or unsubstituted $C_4$-$C_{24}$ alkylene group. In some embodiments, $R^B$ may be a substituted or unsubstituted $C_4$-$C_{12}$ alkylene group. In some embodiments, $R^B$ may include one or more alkyl branching groups. In some embodiments, the branching groups may include a substituted or unsubsituted $C_1$-$C_6$ alkyl group. In some embodiments, the branching groups may include a substituted or unsubsituted $C_1$-$C_4$ alkyl group. In some embodiments, the branching groups may include one or more alkyl branching groups (i.e., secondary alkyl branching groups). In some embodiments, the branching group may be a t-butyl group. In some embodiments the ester may be:

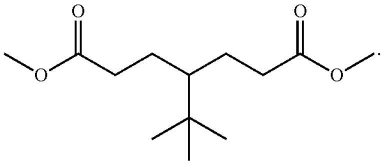.

dimethyl 4-(*tert*-butyl)heptanediote

Illustrative esters also include those of formula ROC(O)CR"C(O)OR', wherein R, R', and R" are individually a substituted or unsubstituted alkyl or alkenyl group. In the formula, R, R', and R" may be individually a substituted or unsubstituted $C_1$-$C_{30}$ alkyl or alkenyl group. In the formula, R, R', and R" may be individually a substituted or unsubstituted $C_1$-$C_{12}$ alkyl or alkenyl group. The ester may be a high permittivity malonate. Some illustrative esters include, but are not limited to, diethyl malonate, diethylethyl malonate, methylethyl malonate, ethylpropyl malonate, dipropyl malonate, and the like, or a mixture of any two or more thereof.

In an illustrative embodiment, the dielectric fluid contains an ester and other materials. For example, the dielectric fluid may include at least one ester and one or more non-ester materials; more than one ester; at least one ester, one or more non-ester materials, and one or more additives, etc. The ester may include additional functional groups. In an illustrative embodiment, the dielectric fluid may include multiple esters. In yet other embodiments, the dielectric fluid may be multiple esters with other materials (e.g., non-esters and/or additives).

In an illustrative embodiment, esters such as pentyl propionate ($C_8H_{16}O_2$) may be used as the dielectric fluid. For example, pentyl propionate can be economical and commercially available in highly pure grades (e.g., ≥99% pure). In some embodiments, such as those with small electrode gaps (e.g., ≤0.5 mm), pentyl propionate has an inherent breakdown voltage of ≥10 kV/mm. The density is relatively low, which reduces the overall weight of the electrostatic machine. The viscosity of pentyl propionate is relatively low (e.g., 1.04 cP) and has a wide liquid temperature range (>−75° C. to 165° C.). In some instances, purification via drying and distillation is a simple and straightforward process. Pentyl propionate is non-toxic and may not have a negative environmental impact. In some instances, ester synthesis techniques can be used to tailor the molecule to maximize torque production in an electrostatic machine.

In an illustrative embodiment, acetate esters (e.g., $CH_3CO_2R$, where R is an organyl group) can be used as the dielectric fluid. Acetate esters can have many of the properties (or have similar properties) explained above with respect to pentyl propionate. In some instances, acetate esters have inoffensive, sweet odors, are inexpensive, and are of low toxicity.

The dielectric fluid may further include a mixture with other dielectric materials such as, but not limited to, acyclic or cyclic carbonates or carbamates, or fluorinated hydrocarbons, or a mixture of any two or more thereof. Illustrative carbonates include, but are not limited to, ethylene carbonate, dimethyl carbonate, diethyl carbonate, ethylmethyl carbonate, dipropyl carbonate, propylene carbonate, methyl butyrate, γ-butyrolactone, N-methylpyrrolidinone, vinylene carbonate, dioxolane, δ-butyrolactone, diethyl ether, or a combination of any two or more thereof has been used. In an illustrative embodiment, pentyl propionate and methyl hexanoate mixture is used. A carboxylic acid can be added to an ester, which may increase the fluid's permittivity.

Cyclic carbonates have a functional group consisting of a carbon atom that is double bonded to an oxygen atom and single bonded to two other oxygen atoms. Alkyl groups are attached to the single bonded oxygen atoms. The alkyl groups do link together such that the molecule forms a ring configuration. Some examples of cyclic carbonates that can be used as a dielectric fluid include ethylene carbonate, propylene carbonate, and vinylene carbonate. In some instances, the cyclic carbonate has an oxygen atom replace by nitrogen, and may be represented as —OC(O)N. In some instances, a methyl group can be attached to the nitrogen atom at the 3 position. For example, the dielectric fluid can comprise 3-methyl-2-oxazolidinone, 3-ethyl-2-oxazolidinone, and/or 3-methyl-1,3-oxazinan-2-one.

In some instances, the carbonate may include a sulfone group. A sulfone has a functional group consisting of a sulfur atom that is double bonded to two different oxygen atoms and has single bonds to two separate alkyl groups. In some instances, the sulfone can be acyclic. For example, the dielectric fluid can include dimethyl sulfone, in which both alkyl substituents are methyl groups. In other instances, the sulfone can be cyclic. For example, the dielectric fluid can include sulfolane, in which the alkyl groups are linked together forming a 5 member ring. In some instances, the dielectric fluid can be dimethyl sulfone, sulfolane or a mixture of dimethyl sulfone and sulfolane. For example, the dielectric fluid has an aromatic structure in which a nitrogen atom is present at a first position in a ring of the aromatic structure and at least one nitrile (CN) group can be a substituent at a second position. In some embodiments, the dielectric fluid may include a nitrile-substituted heteroaromatic solvent.

Illustrative fluorinated hydrocarbons may include those such as, but not limited to, specialty fluids Vertrel XF and Vertrel Sinera produced by E. I. du Pont de Nemours and Company (DuPont), which is a noncyclic fluorinated hydrocarbon with a chemical formula of $C_5H_2F_{10}$. These compounds have physical properties that can be suitable for use as a dielectric fluid in an electrostatic machine. In some embodiments, such as when small electrode gaps are used (e.g., less than 0.38 mm), Vertrel has an inherent breakdown voltage of greater than 20 kilovolts per millimeter (kV/mm). In some embodiments, Vertrel can be suitably pure as commercially available. For example, conductivities of about $10^{12}$ Siemens per centimeter (S/cm) can be commercially available and can be suitable for use in an electrostatic machine. In such an example, a solvent for purification may not be required. The viscosity of Vertrel is relatively low (0.67 cP). Vertrel is nonflammable and has a low toxicity. In other instances, the dielectric fluid can comprise (or can be) other hydrofluorocarbons, such as Novec 7100 produced by 3M. Novec 7100 is a noncyclic fluorinated hydrocarbon with a chemical formula $C_4F_9OCH_3$. Novec 7100 has properties similar to those of Vertrel.

However, Vertrel XF has a relative permittivity of 7.1, and Vertrel Sinera has a relative permittivity of 5, which can generate less torque in an electrostatic machine than fluids with a higher permittivity. Vertrel has a boiling point of 55° C., and, therefore, can be volatile and problematic for elevated working temperatures. In some instances, Vertrel can be used as a dielectric fluid in an electrostatic machine. In other instances, Vertrel can be used as a co-solvent with a fluid that has a relatively high permittivity.

In an illustrative embodiment, a coating may be applied to one or more of the electrodes. The coating may be used to alter the electrode surface properties. For example, the coating may be used to increase the breakdown voltage and/or the electric field between electrodes. In an illustrative embodiment, the electrode may be made of a plastic or other non-conductive material, and the electrode may be coated with a conductive material such as a metal.

In any of the above embodiments, the dielectric fluid may include a drag reducing agent. Drag reducing agents are those materials that will reduce the turbulence within the device. The drag reducing agents may include polymers. Illustrative drag reducing agents include, but are not limited to poly-isobutylene, polyethylene oxide, polyacrylamide; polysaccharides, surfactants, solid particle suspensions, and combinations of any two or more thereof. The drag reducing agent may be incorporated in the dielectric fluid from 1 to 1000 ppm. This includes from 1 to 500 ppm, from 1 to 250 ppm, from 1 to 100 ppm, from 1 to 50 ppm, or from 1 to 10 ppm.

In some instances, one or more fluids have been mixed together to produce a dielectric fluid to be used in an electrostatic machine. The mixture can have a combination of properties that is better than any of its constituent fluids. For example, a mixture of a high permittivity fluid with a low viscosity fluid can have a relatively high permittivity and a relatively low viscosity. In general, some high permittivity fluids are also highly viscous and conductive. In some embodiments, such high permittivity fluids can be mixed with a low permittivity fluid that has low viscosity and low conductivity. The resulting mixture can have a balance of physical properties that can be better suited as a dielectric fluid within an electrostatic machine.

In some embodiments, a passivation layer can be created between electrodes (e.g., rotor plates and stator plates) and the dielectric fluid. In some instances, high permittivity fluids, such as propylene carbonate, can be thermodynamically unstable in a high electric filed. Such fluids can produce a gas that can lower the breakdown voltage, thereby leading to arcing between the electrodes. For example, propylene carbonate can be reduced at a negative electrode to produce propylene gas, and can be oxidized at the positive electrode to produce carbon dioxide gas.

In some embodiments, a passivation layer can be formed on the surface of the electrodes to reduce and/or eliminate gas formation by creating a barrier that hinders electron transfer between the electrode and the fluid. For example, a propylene carbonate based fluid including 6% by volume ethylene sulfite and 0.2% by volume water can be used as a dielectric fluid within an electrostatic machine to create a passivation layer. Ethylene sulfite can form an effective passivation layer on the negative electrode in propylene carbonate based solutions. Doping propylene carbonate with trace amounts of water can form an effective passivation layer on positively charged electrodes. For example, the breakdown voltage of a machine without a passivation layer can be 4.7 kV/mm. With the addition of a passivation layer on the electrodes of the machine, the breakdown voltage can be increased to 9.9 kV/mm. In alternative embodiments, any suitable fluid can be used to create a dielectric fluid for forming a passivation layer on the electrodes. Although ethylene sulfite and water are used in the example above, in alternative embodiments, any suitable additives can be used with propylene carbonate to form a passivation layer on the electrodes. For example, a mixture of 99% by weight propylene carbonate and 1% by weight additives can be used. In other examples, 98.5%, 98%, 95%, 90%, 80%, etc. by weight propylene carbonate can be used.

In some embodiments, a first dielectric fluid can be used to create a passivation layer (e.g., a propylene carbonate based fluid including 6% by volume ethylene sulfite and 0.2% by volume water) and a second dielectric fluid can be used while operating the electrostatic machine (e.g., high purity propylene carbonate). The rotor electrodes and stator electrodes can be immersed in a first dielectric fluid. The first dielectric fluid can fill a gap between stator electrodes and rotor electrodes. In some embodiments, a DC voltage can be applied across the stator electrodes and the rotor electrodes. The first dielectric fluid can react with surfaces of the stator electrodes and rotor electrodes, thereby forming a passivation layer on the electrodes. The first dielectric fluid can be removed from the electrodes. In some instances, the stator electrodes and rotor electrodes can be rinsed with distilled water and dried. In some embodiments, the passivation layer can be produced on the stator electrodes and rotor electrodes while the electrodes are outside of a housing of the electrostatic machine. The stator electrodes and the rotor electrodes can be assembled and placed in the housing. The housing of the electrostatic machine can be filled with the second dielectric fluid. The electrostatic machine can be run as intended with the second dielectric fluid.

In alternative embodiments, any suitable method can be used to provide a passivation layer on electrodes of an electrostatic machine. For example, the electrodes can be covered with carbon (e.g., diamond), silver, ceramic (e.g., $BaTiOP_3$), etc. In yet other embodiments, no passivation layer may be used. In such embodiments, circulation of the dielectric fluid can be sufficient to prevent gas from building up on the electrodes.

Several factors can affect efficiency and power output of electrostatic machines. The force density between stator plates and rotor plates increases with the square of the applied electric field. Such a relationship can be seen in Coulombs law, discussed above. Thus, the applied electric field can be an important factor in creating an efficient and useful electrostatic machine. The permittivity of a fluid can be defined by the maximum electric field that can be applied before breakdown (e.g., arcing). Many factors can affect permittivity of a fluid including the gap size between rotor plates and stator plates, the material of the rotor plates and the stator plates, surface condition of the rotor plates and stator plates, geometry of the rotor plates and stator plates, liquid molecular structure and presence of impurities in the dielectric fluid, the nature of applied voltage, temperature, pressure, and uniformity of the electric field. One or more of such factors can be influenced to maximize permittivity of the fluid.

In some embodiments, increasing the distance between the electrodes (e.g., rotor plates and stator plates) can produce a significant drop in the permittivity. Experimentation with propylene carbonate confirmed that decreasing the gap improves the breakdown voltage until the gap is reduced to below 0.30 millimeters (mm). The permittivity can be largely independent of gap for gap sizes smaller than 0.30 mm. Accordingly, in some embodiments gaps between stator plates and rotor plates in machines can be about 0.30 mm.

Different metals can differ in their ability to donate or receive electrons. Accordingly, the proper pairing of electrodes can produce space-charge effects that can alter the uniformity of the applied electric field and, consequently, can affect the permittivity and ionic conductivity. In some embodiments, aluminum can be used for the negatively charged plates and stainless steel can be used for the positively charged plates with propylene carbonate as the dielectric fluid. Such a configuration can produce a force density of 10 pounds per square inch (psi). By changing the material of the positively charged plates to be aluminum, a force density of 4.5 psi can be produced. Accordingly, in some embodiments, materials of construction for the rotor plates can be different than materials of construction for the stator plates.

In some embodiments, one or more additives can be added to the dielectric fluid. For example, a small amount (e.g., 10% by volume) of 2-pyridine carbonitrile can be added to propylene carbonate. Such a combination has been discovered by experimentation to produce the greatest force density, which was measured at 11.8 psi. The improved efficacy of this mixture can be due to space-charge effects. The improved efficacy can also (or alternatively) be the result of a large cross sectional area and resonance stability, which makes the combination of fluids an effective electron absorber.

Electrostatic machines that are compact and easy to manufacture can increase the utility of such machines. In some instances, compact packaging of an electrostatic machine can be difficult because of the high voltage clearances required of the internal parts (e.g., stator plates and rotor plates) with respect to the housing. Further, seals capable of maintaining a high vacuum within the housing can be mechanically challenging. Because of the clearances needed between stator plates and rotor plates and maintenance of high vacuum, in some instances, electrostatic machines can be bulky and oversized.

However, electrostatic machines that use a dielectric fluid in the gap between the stator plates and the rotor plates may not need a high vacuum within the housing of the machine. Accordingly, the housing can be more compact and thinner, complicated vacuum seals may not be used, and a vacuum pump and associated hoses may not be used. Further, by using a dielectric fluid between the gaps of the stator plates and the rotor plates, the clearances between the stator plates and the rotor plates can be reduced, thereby reducing the size of the machine. Thus, by using a dielectric fluid, in some embodiments, the power density of electrostatic machines can be increased.

Additionally, use of a dielectric fluid can be used as a heat transfer medium. Electrical and mechanical losses (e.g., inefficiencies) can create heat. Excessive heat can further reduce the efficiency of electrostatic machines. As discussed above, in some embodiments, an electrostatic machine can include one or more recirculation paths that can flow dielectric fluid around various parts of the electrostatic machine. Thus, the dielectric fluid can transfer heat from hotter components (e.g., stator plates, rotor plates, shafts, bearings, etc.) to cooler components (e.g., housing). Further, the one or more recirculation paths can include one or more heat exchangers configured to dissipate heat from the dielectric fluid.

Figure 12:
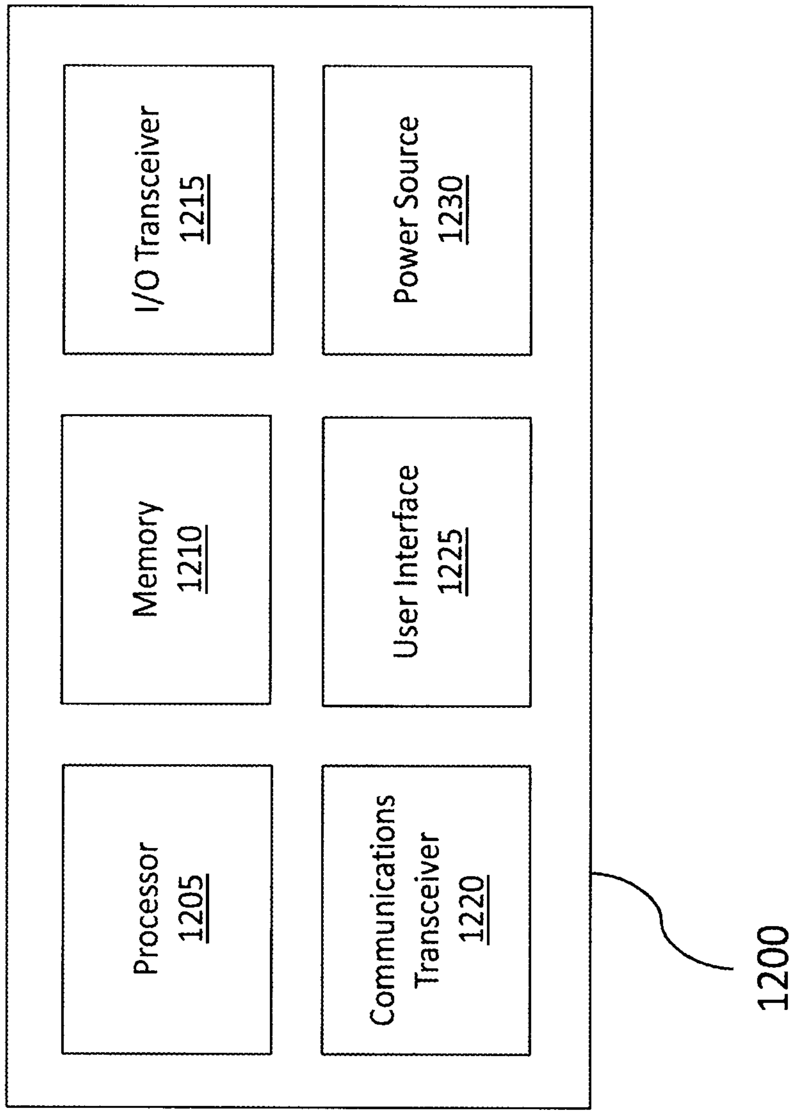
FIG. 12 is a block diagram of a controller in accordance with an illustrative embodiment.

As mentioned above, various aspects of an electrostatic motor system can be controlled, monitored, communicated with, etc. with one or more controllers. FIG. 12 is a block diagram of a controller in accordance with an illustrative embodiment. In alternative embodiments, additional, fewer, and/or different elements may be used. A controller 1200 can include a processor 1205, a memory 1210, an input and/or output (I/O) transceiver 1215, a communications transceiver 1220, a power source 1230, and a user interface 1225. An electrostatic motor system can use one or more controllers 1200 to control and/or monitor various components and/or sensors of the flywheel energy storage system.

In some embodiments, controller 1200 can include processor 1205. Processor 1205 can be configured to carry out and/or cause to be carried out one or more operations described herein. Processor 1205 can execute instructions as known to those skilled in the art. The instructions may be carried out by one or more special purpose computers, logic circuits (e.g., programmable logic circuits (PLC)), and/or hardware circuits. Thus, processor 1205 may be implemented in hardware, firmware, software, or any combination of these methods. The term "execution" is the process of running an application or the carrying out of the operation called for by an instruction. The instructions may be written using one or more programming language, scripting language, assembly language, etc. Processor 1205 executes an instruction, meaning that it performs the operations called for by that instruction. Processor 1205 operably couples with memory 1210, communications transceiver 1220, I/O transceiver 1210, power source 1230, user interface 1225, etc. to receive, to send, and to process information and to control the operations of the controller 1200. Processor 1205 may retrieve a set of instructions from a permanent memory device such as a read-only memory (ROM) device and copy the instructions in an executable form to a temporary memory device that is generally some form of random access memory (RAM). Controller 1200 may include a plurality of processors that use the same or a different processing technology. In an illustrative embodiment, the instructions may be stored in memory 1210.

In some embodiments, controller 1200 can include memory 1210. Memory 1210 can be an electronic holding place or storage for information so that the information can be accessed by processor 1205 as known to those skilled in the art. Memory 1210 can include, but is not limited to, any type of random access memory (RAM), any type of read-only memory (ROM), any type of flash memory, etc. such as magnetic storage devices (e.g., hard disk, floppy disk, magnetic strips, etc.), optical disks (e.g., compact disk (CD), digital versatile disk (DVD), etc.), smart cards, flash memory devices, etc. Controller 1200 may have one or more computer-readable media that use the same or a different memory media technology. Controller 1200 may have one or more drives that support the loading of a memory medium such as a CD, a DVD, a flash memory card, etc.

In some embodiments, controller 1200 can include a communications transceiver 1220. Communications transceiver 1220 can be configured to receive and/or transmit information. In some embodiments, communications transceiver 1220 can communicate information via a wired connection, such as an Ethernet connection, one or more twisted pair wires, coaxial cables, fiber optic cables, etc. In some embodiments, communications transceiver 1220 can communicate information via a wireless connection using microwaves, infrared waves, radio waves, spread spectrum technologies, satellites, etc. Communications transceiver 1220 can be configured to communicate with another device using cellular networks, local area networks, wide area networks, the Internet, etc. In some embodiments, one or more of the elements of controller 1200 communicate via wired or wireless communications.

In some embodiments, controller 1200 can include an I/O transceiver 1215. The I/O transceiver 1215 can be configured to communicate with and/or receive information from one or more sensors, devices, etc. The I/O transceiver 1215 can further be configured to transmit information to switches of a power converter (e.g., switches 910, switches 975, etc.). The I/O transceiver 1215 can be configured to receive information from one or more sensors, such as temperature sensors, pressure sensors, power sensors, voltage sensors, current sensors, torque sensors, etc. The I/O transceiver 1215 can be configured to send and transmit discrete information, analog information, digital information, etc. The I/O transceiver can include multiple cards and/or communication ports.

In some embodiments, controller 1200 can include power source 1230. Power source 1230 can be configured to provide electrical power to one or more elements of controller 1200. In some embodiments, power source 1230 can include an alternating power source, such as available line voltage (e.g., 120 Volts alternating current at 60 Hertz in the United States). Power source 1230 can include one or more transformers, rectifiers, etc. to convert electrical power into power useable by the one or more elements of controller 1200, such as 1.5 V, 8 V, 12 V, 24 V, etc. Power source 1230 can include one or more batteries.

In some embodiments, controller 1200 can include user interface 1225. User interface 1225 can be configured to receive and/or provide information from/to a user. User interface 1225 can be any user interface known in the art. User interface 1225 can be an interface for receiving user input and/or machine instructions for entry into controller 1200 as known to those skilled in the art. User interface 1225 may use various input technologies including, but not limited to, a keyboard, a stylus and/or touch screen, a mouse, a track ball, a keypad, a microphone, voice recognition, motion recognition, disk drives, remote controllers, input ports, one or more buttons, dials, joysticks, etc. to allow an external source, such as a user, to enter information into controller 1200. User interface 1225 can be used to navigate menus, adjust options, adjust settings, adjust display, etc. User interface 1225 can be configured to provide an interface for presenting information from controller 1200 to external systems, users, or memory. For example, user interface 1225 can include an interface for a display, a printer, a speaker, alarm/indicator lights, a network interface, a disk drive, a computer memory device, etc. User interface 1225 can include a color display, a cathode-ray tube (CRT), a liquid crystal display (LCD), a plasma display, an organic light-emitting diode (OLED) display, etc.

In an illustrative embodiment, any of the operations described herein can be implemented at least in part as computer-readable instructions stored on a computer-readable memory. Upon execution of the computer-readable instructions by a processor, the computer-readable instructions can cause a node to perform the operations.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B." Further, unless otherwise noted, the use of the words "approximate," "about," "around," etc., mean plus or minus twenty percent.

In general, as used herein, "substituted" refers to an alkyl, alkenyl, alkynyl, aryl, or ether group, as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group may be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); elements in group 16 of the periodic table (e.g., O, S, Se, Te, etc.); hydroxyls; alkoxy, alkenoxy, alkynoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like. In embodiments in which oxygen (or other elements in group 16 of the periodic table) is used, the oxygen (or group 16 element) provides a source that captivates electrons and increases the negative polarity of the molecule.

As used herein, "alkyl" groups include straight chain and branched alkyl groups having from 1 to about 20 carbon atoms, and typically from 1 to 12 carbons or, in some embodiments, from 1 to 8 carbon atoms. In alternative embodiments, "alkyl" groups include straight chain and branched alkyl groups having greater than 20 carbon atoms, such as up to about 100 carbon atoms. As employed herein, "alkyl groups" include cycloalkyl groups as defined below. Alkyl groups may be substituted or unsubstituted. Examples of straight chain alkyl groups include methyl, ethyl, n-propyl, n-butyl, n-pentyl, n-hexyl, n-heptyl, and n-octyl groups. Examples of branched alkyl groups include, but are not limited to, isopropyl, sec-butyl, t-butyl, neopentyl, and isopentyl groups. Representative substituted alkyl groups may be substituted one or more times with, for example, amino, thio, hydroxy, cyano, alkoxy, and/or halo groups such as F, Cl, Br, and I groups. As used herein the term haloalkyl is an alkyl group having one or more halo groups. In some embodiments, haloalkyl refers to a per-haloalkyl group.

Groups described herein having two or more points of attachment (i.e., divalent, trivalent, or polyvalent) within the present technology are designated by use of the suffix, "ene." For example, divalent alkyl groups are alkylene groups, divalent alkenyl groups are alkenylene groups, and so forth. Nonlimiting examples include methylene ($-CH_2)-$, ethylene ($-CH_2-CH_2-$), ethenylene ($-CH=CH-$), butylene ($-CH_2-CH_2-CH_2-CH_2-$), and butenylene ($-CH=CH-CH_2-CH_2-$). Substituted groups having a single point of attachment to the compound of the present technology are not referred to using the "ene" designation. Thus, e.g., chloroethyl is not referred to herein as chloroethylene.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. An electrostatic machine comprising:

a drive electrode and a stator electrode separated by a gap and forming a capacitor, wherein the drive electrode is configured to move with respect to the stator electrode;

a housing configured to enclose the drive electrode and the stator electrode, wherein the stator electrode is fixed to the housing; and a dielectric fluid that fills a void defined by the housing, the drive electrode, and the stator electrode, wherein the dielectric fluid comprises methyl (E)-5,5-dimethylhex-3-enoate, methyl 5,5-dimethylhexanoate, hexyl isobutyrate, pentyl isobutyrate, isoamyl isovalerate, geranyl acetate, geranyl propionate, pentyl propionate, or a mixture of any two or more thereof.

2. The electrostatic machine of claim 1, wherein the dielectric fluid comprises isoamyl isovalerate.

3. The electrostatic machine of claim 1, wherein the dielectric fluid further comprises a malonate.

4. The electrostatic machine of claim 3, wherein the malonate comprises dimethyl malonate, methylethyl malonate, diethyl malonate, methylpropyl malonate, ethylpropyl malonate, dipropyl malonate, dimethyl methylmalonate, methylethyl methylmalonate, diethyl methylmalonate, methylpropyl methylmalonate, ethylpropyl methylmalonate, dipropyl methylmalonate, dimethyl ethylmalonate, methylethyl ethylmalonate, diethyl ethylmalonate, methylpropyl ethylmalonate, ethylpropyl ethylmalonate, dipropyl ethylmalonate, or a mixture of any two or more thereof.

5. The electrostatic machine of claim 1, wherein the dielectric fluid further comprises dimethyl sulfone, sulfolane, or a mixture of dimethyl sulfone and sulfolane.

6. The electrostatic machine of claim 1, wherein the dielectric fluid further comprises a compound having a carbonate moiety, a nitrile substituted heteroaromatic solvent; a solvent having cyclic structure and a moiety represented as —OC(O)N—, a fluorinated acyclic hydrocarbon, or solvent comprising a sulfonyl group.

7. The electrostatic machine of claim 1, wherein the dielectric fluid further comprises a nitrile substituted heteroaromatic solvent.

8. The electrostatic machine of claim 1, wherein the dielectric fluid further comprises 3-methyl-2-oxazolidinone, 3-ethyl-2-oxazolidinone, or 3-methyl-1,3-oxazinan-2-one.

9. The electrostatic machine of claim 1, wherein the dielectric fluid further comprises ethylene carbonate, dimethyl carbonate, diethyl carbonate, ethylmethyl carbonate, dipropyl carbonate, propylene carbonate, methyl butyrate, γ-butyrolactone, N-methylpyrrolidinone, vinylene carbonate, dioxolane, δ-butyrolactone, diethyl ether, or a mixture of any two or more thereof.

10. The electrostatic machine of claim 1, wherein the dielectric fluid further comprises a drag reducing agent selected from the group consisting of poly-isobutylene, polyethylene oxide, polyacrylamide, polysaccharides, surfactants, solid particle suspensions, and a combination of any two or more thereof.

11. The electrostatic machine of claim 1, wherein the dielectric fluid further comprises a compound of formula $R^C-O(O)CHR^BC(O)O-R^A$, wherein $R^A$ and $R^C$ are individually a substituted or unsubstituted alkyl or alkenyl group and $R^B$ is a substituted or unsubstituted alkylene group.

12. The electrostatic machine of claim 11, wherein $R^A$ and $R^C$ are individually a substituted or unsubstituted $C_1$-$C_6$ alkyl group.

13. The electrostatic machine of claim 12, wherein $R^A$ and $R^C$ are methyl.

14. The electrostatic machine of claim 11, wherein $R^B$ is a substituted or unsubstituted $C_4$-$C_{24}$ alkylene group.

15. The electrostatic machine of claim 11, wherein $R^B$ is a substituted or unsubstituted $C_4$-$C_{24}$ branched alkylene group.

16. The electrostatic machine of claim 15, wherein $R^B$ is t-butyl.

17. The electrostatic machine of claim 15, wherein the compound of formula $R^C-O(O)CHR^BC(O)O-R^A$ is:

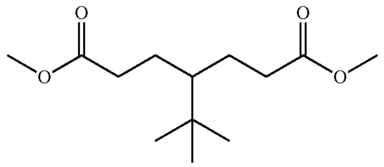

dimethyl 4-(*tert*-butyl)heptanediote

* * * * *